(12) United States Patent
Tornero Garcia et al.

(10) Patent No.: US 9,561,190 B2
(45) Date of Patent: Feb. 7, 2017

(54) NONWOVEN MEMBRANE AS A DRUG DELIVERY SYSTEM

(71) Applicants: UNIVERSITAT POLITECNICA DE CATALUNYA, Barcelona (ES); HOSPITAL SANT JOAN DE DEU, Esplugues de Llobregat (ES)

(72) Inventors: José Antonio Tornero Garcia, Terrasa (ES); Angel Montero Carcaboso, Esplugues de Llobregat (ES); Joan Bertran I Llavina, Arenys de Mar (ES)

(73) Assignees: UNIVERSITAT POLITECNICA DE CATALUNYA, Barcelona (ES); HOSPITAL SANT JOAN DE DEU, Esplugues de Llobregat (ES)

(*) Notice: Subject to any disclaimer, the term of this patent is extended or adjusted under 35 U.S.C. 154(b) by 0 days.

(21) Appl. No.: 14/389,330

(22) PCT Filed: Mar. 27, 2013

(86) PCT No.: PCT/EP2013/056522
§ 371 (c)(1),
(2) Date: Sep. 29, 2014

(87) PCT Pub. No.: WO2013/144206
PCT Pub. Date: Oct. 3, 2013

(65) Prior Publication Data
US 2015/0072008 A1    Mar. 12, 2015

(30) Foreign Application Priority Data
Mar. 30, 2012    (EP) .................................... 12162338

(51) Int. Cl.
*A61K 9/70* (2006.01)
*A61K 9/00* (2006.01)
(Continued)

(52) U.S. Cl.
CPC ........... *A61K 9/7007* (2013.01); *A61K 9/0024* (2013.01); *A61K 9/70* (2013.01); *A61K 31/4745* (2013.01);
(Continued)

(58) Field of Classification Search
CPC ........ A61K 9/0024; A61K 47/34; A61K 9/70; A61K 9/7007; A61K 31/4745; D01D 5/0007; D01D 5/003; D01D 10/00; D01F 11/08; D04H 1/728; D04H 3/016; D10B 2331/041; D10B 2509/00; A61M 35/00
(Continued)

(56) References Cited

U.S. PATENT DOCUMENTS

2002/0096246 A1* 7/2002 Sennet ................... B01D 39/04
156/167
2005/0158362 A1* 7/2005 Wheatley ............. A61K 9/0009
424/426
(Continued)

FOREIGN PATENT DOCUMENTS

WO    WO 2008013713    1/2008
WO    WO 2008067145    6/2008
(Continued)

OTHER PUBLICATIONS

Xie et al. ("Release modulation and cytotoxicity of hydroxycamptothecin-loaded electrospun fibers with 2-hydroxypropyl-_-cyclodextrin inoculations" in International Journal of Pharmaceutics, 391, (2010) pp. 55-64).*
(Continued)

*Primary Examiner* — Blessing M Fubara
(74) *Attorney, Agent, or Firm* — Squire Patton Boggs (US) LLP

(57) ABSTRACT

The invention defines a nonwoven membrane for the controlled and sustained release of a therapeutic or cosmetic
(Continued)

active agent in the area of the body to be treated. This nonwoven membrane comprises one single type of biocompatible electrospun nanofibers and microparticles of at least one therapeutic or cosmetic active agent which are entangled between the nanofibers, the active agent having a low water solubility.

21 Claims, 10 Drawing Sheets

(51) Int. Cl.
| | |
|---|---|
| D01D 5/00 | (2006.01) |
| D01D 10/00 | (2006.01) |
| D01F 11/08 | (2006.01) |
| A61K 47/34 | (2006.01) |
| A61K 31/4745 | (2006.01) |
| A61M 35/00 | (2006.01) |
| D04H 1/728 | (2012.01) |
| D04H 3/016 | (2012.01) |
| D04H 5/02 | (2012.01) |

(52) U.S. Cl.
CPC .............. *A61K 47/34* (2013.01); *A61M 35/00* (2013.01); *D01D 5/003* (2013.01); *D01D 5/0007* (2013.01); *D01D 10/00* (2013.01); *D01F 11/08* (2013.01); *D04H 1/728* (2013.01); *D04H 3/016* (2013.01); *D04H 5/02* (2013.01); *D10B 2331/041* (2013.01); *D10B 2509/00* (2013.01)

(58) Field of Classification Search
USPC ... 424/486, 488; 514/283; 264/484; 604/289
See application file for complete search history.

(56) References Cited

U.S. PATENT DOCUMENTS

| | | | |
|---|---|---|---|
| 2006/0083784 A1* | 4/2006 | Ignatious | A61K 9/146 424/464 |
| 2006/0094320 A1 | 5/2006 | Chen et al. | |
| 2008/0311205 A1* | 12/2008 | Habib | A61K 9/1652 424/488 |

FOREIGN PATENT DOCUMENTS

| | | |
|---|---|---|
| WO | WO 2009064767 | 5/2009 |
| WO | WO 2009133059 | 11/2009 |
| WO | WO 2010096254 | 8/2010 |

OTHER PUBLICATIONS

Liang et al., "Functional electrospun nanofibrous scaffolds for biomedical applications" in Advanced Drug Delivery Reviews 59 (2007) 1392-1412.*
Zhang et al., "Recent development of polymer nanofibers for biomedical and biotechnological applications" in Journal of Materials Science: Materials in Medicine 16 (2005) 933-946.*
Verreck et al., "Incorporation of drugs in an amorphous state into electrospun nanofibers composed of a water-insoluble, nonbiodegradable polymer," in Journal of Controlled Release 92 (2003) 349-360.*
International Search Report for PCT/EP2013/056522.
Attenello et al., Use of Gliadel (BCNU) Wafer in the Surgical Treatment of Malignant Glioma: A 10-Year Institutional Experience. Ann. Surg. Oncol., 2008 15(10):2887-93.
Liu et al., The nanofibrous architecture of poly(L-lactic acid)-based functional copolymers, Biomaterials 31 (2010) 259-269.
Xie et al., Electrospun micro- and nanofibers for sustained delivery of paclitaxel to treat C6 glioma in vitro, Pharm. Res. 23 (2006), 1817-1826 ).
Xu et al., BCNU-loaded PEG-PLLA ultrafine fibers and their in vitro antitumor activity against Glioma C6 cells, Journal of Controlled Release 114 (2006) 307-316.
Patel et al., Bioactive nanofibers: synergistic effects of nanotopography and chemical signaling on cell guidance, Nano Lett. 7 (2007) 2122-8.
Bolgen et al., In vivo performance of antibiotic embedded electrospun PCL membranes for prevention of abdominal adhesions, J. Biomed. Mater. Res. B Appl. Biomater. 81 B(2007) 530-543.
Cai et al., International Journal of Pharmaceutics 419 (2011) 240-246.
Wang et al., Fabrication and Characterization of Prosurvival Growth Factor Releasing, Anisotropic Scaffolds for Enhanced Mesenchymal Stem Cell Survival/Growth and Orientation, Biomacromolecules 2009, 10, 2609-2618.

* cited by examiner

NONWOVEN MEMBRANE AS A DRUG DELIVERY SYSTEM

FIELD OF THE INVENTION

The invention relates to the field of drug delivery systems (DDS). In particular, the invention relates to a nonwoven membrane for the controlled and sustained release of a therapeutic or cosmetic active agent in the area of the body to be treated. This nonwoven membrane comprises one single type of biocompatible electrospun nanofibers and microparticles of a pure active agent which are entangled between the nanofibers, the active agent having limited water solubility.

BACKGROUND OF THE INVENTION

Drug delivery systems for cancer therapeutics have now been used by millions of patients and have resulted in the creation of new therapies and the improvement of existing ones. Cancer drugs can cause enormous toxicity at the systemic concentrations needed to achieve antitumor activity; therefore, their local delivery creates the possibility of improving both their safety and efficacy.

Consequently, locally implanted polymeric devices have gathered clinical interest during the last decades. One example is provided by the carmustine-loaded wafers for the treatment of gliomas. Such formulations consist in solid discs of the drug carmustine (BCNU) loaded in the polyanhidride polymer poly-[bis(p-carboxyphenoxy)propane sebacic acid. BCNU-loaded wafers are approved for the treatment of brain tumors (gliomas) after surgery (Attenello et al., Use of Gliadel (BCNU) Wafer in the Surgical Treatment of Malignant Glioma: A 10-Year Institutional Experience. *Ann. Surg. Oncol.*, 2008 15(10):2887-93).

Polymeric nanofibers have been proposed as malleable platforms for tissue engineering and as carriers to deliver therapeutic agents locally at specific sites of application. Such nanofiber-based systems combine several important aspects, such as large surface area and high porosity which facilitate permeability to water and diffusion of active agents incorporated into the nanofibers. Three distinct techniques have been proven successful in routinely creating nanofibrous structures: (i) self-assembly, (ii) phase separation and (iii) electrospinning.

Self-assembly, as such used to synthesize nanofibers from peptide amphiphiles is attractive because of the mild condition of fabrication and the small size attainable. Patent application WO 2008/067145 provides a method for nanofiber formation from self-assembling peptides. However, this technique is amenable only to a limited repertoire of polymers and difficult to process into a macroscopic structure. It is also challenging to obtain a sustained release kinetics from these small fibers.

The phase separation technique requires gelation of the polymer and extraction of solvent and suffers from a lack of control over fiber arrangement. The required solvent extraction step would also prematurely leach out any drugs entrapped in the fibers. Additionally, only a few polymers are appropriate for this method and it is strictly a laboratory scale technique (Liu et al., The nanofibrous architecture of poly(L-lactic acid)-based functional copolymers, Biomaterials 31 (2010) 259-269).

The electrospinning technique improves the aforementioned methods to obtain nanofibers because it facilitates the scaling-up of the technique and avoids the solvent extraction step. Electrospun nanofibers for biomedical applications have attracted a great deal of attention in the past several years. For example, electrospun nanofibers have been used in tissue engineering, immobilized enzymes and catalyst, wound dressing and artificial blood vessels. They have also been used as barriers for the prevention of post-operative induced adhesion and vehicles for controlled drug delivery systems.

Both mono-axial and co-axial electrospun nanofibers have been reported to incorporate and release antibiotics, drugs and proteins in a sustained manner. Drugs and bioactive agents are encapsulated, embedded or incorporated within the bulk phase of the fibers, so that their release kinetics depends on their diffusion out of the fiber and the fiber degradation/erosion. For example, in Xie et al., (Xie et al., Electrospun micro- and nanofibers for sustained delivery of paclitaxel to treat C6 glioma in vitro, *Pharm. Res.* 23 (2006), 1817-1826) a biodegradable polymer solution containing hydrophobic anti-cancer drugs such as paclitaxel was directly electrospun to produce drug releasing nanofibrous mesh. Also, Xu et al. (Xu et al., BCNU-loaded PEG-PLLA ultrafine fibers and their in vitro antitumor activity against Glioma C6 cells, *Journal of Controlled Release* 114 (2006) 307-316) developed implantable BCNU-loaded polymer fibers for the controlled release of BCNU. This antineoplasic agent was well incorporated and dispersed uniformly in biodegradable poly(ethylene glycol)-poly(lactic acid) (PEG-PLLA) copolymers nanofibers by using the electrospinning method. In patent application WO 2009/064767 an antimicrobial nanofiber is formed from an electroprocessed blend of cellulose acetate as a polymer material, chlorhexidine (CHX) as an antimicrobial agent and an organic titanate as a crosslinker in such a way that CHX was covalently linked to the nanofiber. Patent application WO 2009/133059 discloses nanofiber matrices formed by electrospinning a solution of a hyperbranched polyester and creatine monohydrate for the controlled release of creatine.

However, many interesting bioactive agents are protein or nucleic acid in nature that do not dissolve in organic solvent and may suffer loss of bioactivity when dispersed in the polymer solution. Co-axial electrospinning, where the drug is dissolved in an aqueous core solution and the polymer in an organic shell solution, is one approach to overcome this drawback by extruding the core and shell solutions individually through two concentric nozzles. In patent application WO 2008/013713 coaxial electrospun nanofibers are disclosed having a core and a polymeric shell surrounding the core, wherein a growth factor or an adenovirus is encapsulated within the core.

In some cases, surfaces of electrospun nanofibers can be chemically functionalized for achieving sustained delivery through physical adsorption of diverse bioactive molecules such as proteins, enzymes, growth factors or drugs. For example, therapeutic proteins and nucleic acid were physically immobilized for controlled delivery (Patel et al., Bioactive nanofibers: synergistic effects of nanotopography and chemical signaling on cell guidance, *Nano Lett.* 7 (2007) 2122-8), and antibacterial agents were physically immobilized for immediate release from the nanofiber surface (Bolgen et al., In vivo performance of antibiotic embedded electrospun PCL membranes for prevention of abdominal adhesions, *J. Biomed. Mater. Res. B Appl. Biomater.* 81B (2007) 530-543).

In recent times, Cai et al. (Cai et al., *International Journal of Pharmaceutics* 419 (2011) 240-246) have proposed the sustained release of 5-fluorouracil (5-FU) by incorporating it into sodium carboxymethylcellulose sub-micron fibers prepared by freeze-drying as an alternative of electrospun nanofibers. The drug release from this swellable matrix is mainly based on diffusion out of the fibers. A similar system was proposed in patent application US 2005/0158362A1, in which bioactive compounds such as bovine serum albumin are suspended or solved in the polymer solution prior to electrospinning, resulting in a system with active agent mainly loaded within the nanofibers.

Because release from active agent-loaded polymer fibers is highly dependent on the composition of the fibers, the active agent-to-polymer ratio, the co-loading of other substances and the thickness of the fibers, newer approaches have been developed that load the active agent in polymer microspheres that control their release from the fiber mesh. Patent WO 2010/096254 developed formulations in which bovine serum albumin (BSA) or chondroitin sulfate are loaded in polystyrene (PS or PLGA) microspheres and then loaded in nanofibers made of electrospun polycaprolactone (PCL) and poly(ethylene oxide) (PEO). The PS microspheres can reside within one fiber or adjacent to a first type-fiber, a second type-fiber or both. The release kinetics of BSA depends upon its diffusion out the corresponding fiber, the degradation of this fiber as well as the degradation of the polymeric microsphere shell.

Recently, Wang et al. (Wang et al., Fabrication and Characterization of Prosurvival Growth Factor Releasing, Anisotropic Scaffolds for Enhanced Mesenchymal Stem Cell Survival/Growth and Orientation, *Biomacromolecules* 2009, 10, 2609-2618) have developed nanofiber scaffolds for tissue engineering that release a insulin growth factor (IGF-1) to induce cellular growth and survival. Such scaffolds are formed by electrospinning polyurethanurea nanofibers and IGF-1-loaded microspheres assembled into the scaffold. Encapsulation of growth factors protects them from proteolysis and allows their sustained release; the release kinetics are dependent upon polymer concentration, molecular weight and growth factor loading in microspheres.

However, the process of manufacturing nanofibers loaded with polymer microspheres containing active agents is challenging because of the complex technical processes required for microsphere production, isolation, sterilization and loading within the nanofiber mesh. In addition, the encapsulation efficiency of the active agent into the microspheres is usually suboptimal. The stability of the active principle can also be affected by solvents used during the microencapsulation process. So there continues to be a need in the state of the art to provide alternative local drug delivery systems for the sustained and controlled delivery of therapeutic agents.

The present inventors have discovered that when active principles are formulated as microparticles of the pure active principle and are entangled between the fiber mesh of a nonwoven membrane of biocompatible electrospun nanofibers, they can be locally released in a sustained way. That is, the microparticles prepared are suspended in a nonsolvent and poured into the nanofiber mesh. As a result, they are physically retained in the membrane between the nanofibers and cannot be released to the external medium but in their solubilised form. Such approach is especially appropriate for active principles of limited water solubility. Release occurs when the physiological fluids fill the membrane and solubilize the microparticles once located in the body area to be treated. Even though the active agent particles are not protected by a polymeric shell like the drug-loaded microsphere of the state of the art, they can be released in a sustained, efficient and oriented manner.

OBJECT OF THE INVENTION

Therefore an object of the present invention is to provide a nonwoven web comprising one single type of biocompatible electrospun nanofibers and microparticles of at least one therapeutic or cosmetic active agent in pure form entangled between the nanofibers, wherein the therapeutic or cosmetic active agent has a water solubility lower than 33 mg/mL. It is very important to highlight that the therapeutic or cosmetic active agent is placed between the nanofibers and not into them. These feature is very important since the release rate in the nonwoven membrane of the present invention is dependent on the solubility of the therapeutic or cosmetic active agent rather than in the solubility or degradation rate of the nanofiber.

Another object of the invention is to provide a taylor-made suit comprising the nonwoven membrane.

Another object of the invention is to provide a method for obtaining the nonwoven membrane.

Another object of the invention is to provide the use of the nonwoven membrane and of the taylor-made suit comprising it.

DETAILED DESCRIPTION OF THE INVENTION

Figure 1:
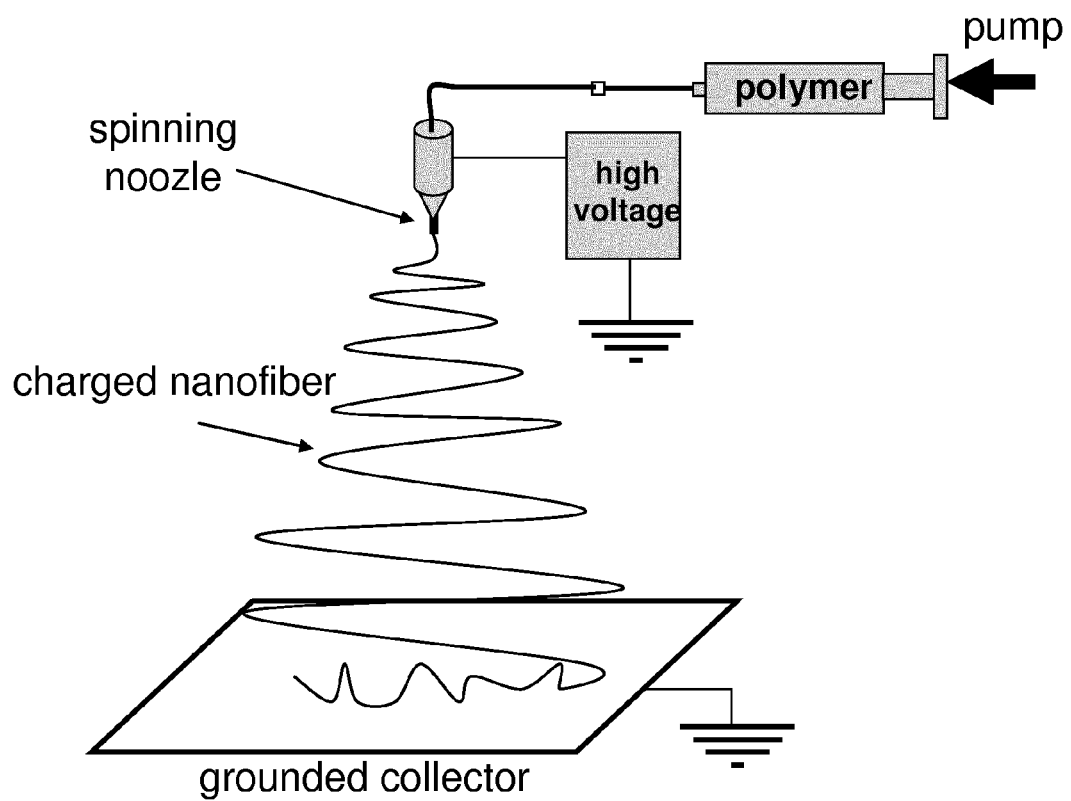
FIG. 1 shows an scheme of the electrospinning process for obtaining the nonwoven membrane of the invention.

The present invention provides a nonwoven membrane comprising one single type of biocompatible electrospun nanofibers and microparticles of at least one therapeutic or cosmetic active agent in pure form entangled between (not within) the nanofibers, wherein the therapeutic or cosmetic active agent has a water solubility lower than 35 mg/mL (thereafter "the nonwoven membrane of the invention").

In the context of the invention the expression "nonwoven membrane" relates to one or more polymeric electrospun nanofibers deposited arbitrarily onto a solid surface (collector) and optionally entangled by one or more of the following methods: physical methods such as adhesion with biocompatible glue, melting or solvent excess, and mechanic methods such as needle punch, hydroentanglement and neumatic entanglement.

As known by the skilled person, electrospinning is a highly versatile technique which combines the use of two techniques namely electrospray and spinning. In the electrospinning process, a polymer solution held by its surface tension at the end of a capillary tube is subjected to an electric field and an electric charge is induced on the liquid surface due to this electric field. When the electric field applied reaches a critical value, the repulsive electrical forces overcome the surface tension forces. Eventually, a charged jet of the solution is ejected from the tip of the Taylor cone and an unstable and a rapid whipping of the jet occurs in the space between the capillary tip and collector which leads to evaporation of the solvent, leaving a polymer behind and leading to a mat of nanofibers deposited on a collector. The electrospinning process is controlled by a number of parameters, usually classified as: solution parameters, process parameters and environment parameters. Solution parameters include viscosity, conductivity, molecular mass and surface tension. Process parameters include the electric field applied, distance between capillary tube and collector and solution flow rate. Each one of these parameters has a significant influence on the morphology of fibers obtained by electrospinning process, and through proper manipulations of these parameters it could be possible to produce nanofibers with desirable morphology and diameters. Furthermore, the environment parameters include relative humidity and room temperature, which also have an important role on the morphology and diameters of electrospun fibers.

In the context of the invention the expression "at least one active agent" means that the microparticles can be microparticles of one or more active agents.

In the context of the invention, "therapeutic agent" relates to molecules that are active against human or veterinary diseases.

In the context of the invention, "cosmetic agent" relates to molecules or substances applied locally to achieve effects perceived as beneficial in cosmetic terms by the subject receiving them.

Also, in the context of the invention the expression "microparticles of at least one active agent in pure form" relates to the fact that the active agent has minimum or no impurities and to the fact that the microparticles have no other component but the active agent, having minimum or no impurities. Therefore, in the context of the invention the microparticle core does not contain any polymeric compound.

In the context of the invention, the term "active agent" refers to a therapeutic agent such as a chemotherapeutic agent, an antibiotic, an antifungal or a nutraceutical, for example, or refers to an active protein such as a growth factor. In any case, it should have a water solubility lower than 33 mg/mL.

In the context of the invention the expression "entangled between the nanofibers" relates to the fact that microparticles are free between the nanofibers but entrapped, that is, physically retained in such a way that they cannot be released but in their solubilised form.

In the context of the invention, the therapeutic or cosmetic active agent has a water solubility lower than mg/mL, that is, the active agent is practically insoluble, very slightly soluble, slightly soluble or sparingly soluble in water according to the standards of the art. These standards can be those of Sigma Aldrich, for example, which are the followings:

| Description | Approximate Volume (mL) of Solvent Needed to Dissolve 1 g of Solute | Solubility in mg/mL |
| --- | --- | --- |
| Very Soluble | Less than 1 | Greater than 1000 |
| Freely Soluble | 1 to 10 | 100-1000 |
| Soluble | 10 to 30 | 33-100 |
| Sparingly Soluble | 30 to 100 | 10-33 |
| Slightly Soluble | 100 to 1000 | 1-10 |
| Very Slightly Soluble | 1000 to 10,000 | 0.1-1 |
| Practically Insoluble | Greater than 10,000 | Less than 0.1 |

In a particular embodiment of the nonwoven membrane of the invention, the therapeutic or cosmetic active agent has a water solubility of 0.001-33 mg/mL.

In a preferred embodiment of the nonwoven membrane of the invention, the therapeutic or cosmetic active agent has a water solubility of 10-33 mg/mL. In another preferred embodiment of the nonwoven membrane of the invention, the therapeutic or cosmetic active agent has a water solubility of 1-10 mg/mL. In another preferred embodiment of the nonwoven membrane of the invention, the therapeutic or cosmetic active agent has a water solubility of 0.1-1 mg/mL. In another preferred embodiment of the nonwoven membrane of the invention, the therapeutic or cosmetic active agent has a water solubility lest than 0.1 mg/mL. In another preferred embodiment of the nonwoven membrane of the invention, the therapeutic or cosmetic active agent has a water solubility of 0.1-0.01 mg/mL. In another preferred embodiment of the nonwoven membrane of the invention, the therapeutic or cosmetic active agent has a water solubility of 0.01-0.001 mg/mL.

In a particular embodiment, the nonwoven membrane consists of biocompatible one single type of electrospun nanofibers and microparticles of at least one active agent in pure form entangled between the nanofibers, wherein the active agent has a water solubility lower than 33 mg/mL.

In other particular embodiment of the nonwoven membrane of the invention, it comprises at least a first layer comprising one single type of biocompatible electrospun nanofibers, a second layer comprising one single type of biocompatible electrospun nanofibers and microparticles of at least one therapeutic or cosmetic active agent entangled between the nanofibers; and a third layer comprising one single type of biocompatible electrospun nanofibers.

In a preferred embodiment of nonwoven membrane of the invention, it comprises one first layer comprising one single type of biocompatible electrospun nanofibers, one second layer comprising one single type of biocompatible electrospun nanofibers and microparticles of at least one therapeutic or cosmetic active agent entangled between the nanofibers; and one third layer comprising biocompatible one single type of electrospun nanofibers.

In a most preferred embodiment, the nonwoven membrane of the invention consists of one first layer comprising one single type of biocompatible electrospun nanofibers, one second layer comprising one single type of biocompatible electrospun nanofibers and microparticles of at least one therapeutic or cosmetic active agent entangled between the nanofibers; and one third layer comprising one single type of biocompatible electrospun nanofibers.

The at least first layer, second layer and third layer of the nonwoven membrane of the invention can have equal or different nanofiber diameters, equal or different thickness and/or can comprise nanofibers made of equal or different biocompatible polymers. Also, when the nonwoven membrane comprises more than one second layer, the possible second layers can comprise microparticles of different therapeutic or cosmetic active agents.

Therefore, in a particular embodiment of nonwoven membrane of the invention, it comprises a first layer comprising one single type of biocompatible electrospun nanofibers, a second layer comprising one single type of biocompatible electrospun nanofibers and microparticles of at least one first therapeutic or cosmetic active agent entangled between the nanofibers; a second layer comprising one single type of biocompatible electrospun nanofibers and microparticles of at least one therapeutic or cosmetic second active agent entangled between the nanofibers; and a third layer comprising one single type of biocompatible electrospun nanofibers.

Optionally, the nonwoven membrane of the invention as previously defined can be coated on one side in order to achieve an unidirectional release towards one face of the membrane. In a particular embodiment, the nonwoven membrane of the invention is coated on one side. The coating of one side of the membrane will be performed by one of the following methods: adhesion with biocompatible glue, contact with polymer solvent (methylene chloride, chlorophorm, ethyl acetate, acetone, dimethylformamide, dimethylsulfoxide, for example), mechanical punch, or electrospinning parameters that favor fiber adhesion.

In a particular embodiment of the nonwoven membrane of the invention, the microparticles of at least one therapeutic or cosmetic active agent in pure form are microcrystals.

The microcrystals of therapeutic or cosmetic active agent can be formed by building particles up from the molecular state, as in precipitation, or by breaking larger particles down, as in milling. In the present invention microcrystals are preferably prepared by the precipitation method, either by solvent incompatibility or pH-dependent crystallization. However, there are other techniques that can be used to obtain the microparticles according to the invention. Active protein microparticles, for example, can be obtained by lyophilisation. This late approach can be useful for obtaining growth factor microparticles having a water solubility lower than 33 mg/mL. In any case, the microparticles or micron-sized solid forms of the invention can be in crystalline state, in amorphous state or in a combination thereof, depending on the growth rate of them, which depends on turn upon temperature and supersaturation conditions. These microparticles are then employed in form of a suspension to prepare the nonwoven membrane of the invention, as stated below.

The suspensions of microparticles for being used in the preparation of the nonwoven membrane of the invention have a particle-size distribution, ranging the mean particle size from 0.1 μm to 20 μm. Therefore, in a particular embodiment of the nonwoven membrane of the invention, the microparticles of the at least one therapeutic or cosmetic active agent have a mean diameter of 0.1-20 μm. In a preferred embodiment of the nonwoven membrane of the invention, the microparticles have a mean diameter of 3-10 μm. In another preferred embodiment of the nonwoven membrane of the invention, the microparticles have a mean diameter of 0.5-5 μm.

As previously defined, the active agent to be included in the nonwoven membrane of the invention can be a therapeutic agent, a cosmetic agent or an active protein having a water solubility lower than 33 mg/mL. More in particular, the active agent can be a therapeutic agent such as a chemotherapeutic agent, a nutraceutical, an antibiotic or an antifungal, for example. Alternatively, the active agent can be an active protein such as a growth factor, for example. As chemotherapeutic agents the following can be cited: SN-38 (7-ethyl-10-hydroxycamptothecin), paclitaxel, cisplatin, carboplatin, etoposide, carmustine, melphalan, camptothecin, 5-fluorouracile, methotrexate, erlotinib, gefitinib, sunitinib, vandetanib, dasatinib, lapatinib, nutlin, gemcitabine, docetaxel, bortezomib, valproic acid, vismodegib, cinacalcet, trabectedin, topotecan, MLN4924, olaparib, iniparib, arsenic trioxide, crizotinib, celecoxib, perifosine, rapamycin, temsirolimus and everolimus. As nutraceuticals the following can be cited: curcumin, resveratrol, genistein and quercetin. Also as antibiotics or as antifungals the following can be cited: chloramphenicol, Penicillin G Procaine, fusidic acid, mebendazol and albendazol. As growth factors the following can be cited: PDGF, TGF-B, EGF, VEGF, IGF-I, bFGF and HGF.

In a particular embodiment of the nonwoven membrane of the invention, the active agent is a therapeutic agent selected from a chemotherapeutic agent and a nutraceutical. In a preferred embodiment of the nonwoven membrane of the invention, the active agent is a chemotherapeutic agent, preferably SN-38, paclitaxel, vandetanib, nutlin or bortezomib. In another preferred embodiment of the nonwoven membrane of the invention, the active agent is a nutraceutical, preferably quercetin, resveratrol, curcumin or genistein. In another preferred embodiment of the nonwoven membrane of the invention, the active agent is a growth factor, preferably PDGF, TGF-B, EGF, VEGF, IGF-I, bFGF or HGF.

In a particular embodiment, the nonwoven membrane of the invention comprises two active agents.

In the nonwoven membrane of the invention, the biocompatible electrospun nanofibers can be made of any suitable biocompatible and biodegradable polymer of the art. This can be a polyester, a polyanhidride, a polyphosphazene, a polyether, etc.

In a particular embodiment of the nonwoven membrane of the invention, the biocompatible electrospun nanofibers are composed of one single type of biocompatible and biodegradable polymer selected from poly-glycolic acid, poly-D,L-lactic acid, poly-D,L-lactide-co-glicolide acid, polycaprolactone, polydioxanone, polyvinylalcohol, collagen, cellulose, hyaluronic acid and a combination thereof. In a particular embodiment of the nonwoven membrane of the invention, the biocompatible electrospun nanofibers are composed of poly-D,L-lactic acid (PLA).

In a particular embodiment, the nonwoven membrane of the invention comprises biocompatible electrospun nanofibers made of PLA and microparticles of at least one therapeutic or cosmetic active agent in pure form entangled between the nanofibers, wherein the active agent has a water solubility lower than 33 mg/mL. In another particular embodiment, the nonwoven membrane of the invention comprises one single type biocompatible electrospun nanofibers and microparticles of at least one therapeutic or cosmetic active agent in pure form entangled between the nanofibers, wherein one of the active agents is SN-38. In a preferred embodiment, the nonwoven membrane of the invention comprises biocompatible electrospun nanofibers made of PLA and microparticles of at least one active agent in pure form entangled between the nanofibers, wherein one of the active agents is SN-38.

In a particular embodiment of the nonwoven membrane of the invention, the at least one therapeutic or cosmetic active agent is loaded in a percentage of 0.001-20% by weight with respect to the total weight of the nonwoven membrane. In a preferred embodiment of the nonwoven membrane of the invention, the at least one therapeutic or cosmetic active agent is loaded in a percentage of 0.5-5% by weight with respect to the total weight of the nonwoven membrane. In a most preferred embodiment of the nonwoven membrane of the invention, the at least one therapeutic or cosmetic active agent is loaded in a percentage of 0.75% by weight with respect to the total weight of the nonwoven membrane.

In a particular embodiment, the nonwoven membrane of the invention comprises biocompatible electrospun nanofibers made of PLA and microparticles of at least one active agent in pure form entangled between the nanofibers, wherein the active agent has a water solubility lower than 33 mg/mL and is loaded in a percentage of 0.001-20% by weight with respect to the total weight of the nonwoven membrane. In another particular embodiment, the nonwoven membrane of the invention comprises one single type of biocompatible electrospun nanofibers and microparticles of at least one therapeutic or cosmetic active agent in pure form entangled between the nanofibers, wherein one of the therapeutic or cosmetic active agents is SN-38 and is loaded in a percentage of 0.001-20% by weight with respect to the total weight of the nonwoven membrane. In a preferred embodiment, the nonwoven membrane of the invention comprises biocompatible electrospun nanofibers made of PLA and microparticles of at least one therapeutic or cosmetic active agent in pure form entangled between the nanofibers, wherein one of the therapeutic or cosmetic active agents is SN-38 and is loaded in a percentage of 0.001-20% by weight with respect to the total weight of the nonwoven membrane.

In a particular embodiment, the nonwoven membrane of the invention comprises biocompatible electrospun nanofibers made of PLA and microparticles of at least one therapeutic or cosmetic active agent in pure form entangled between the nanofibers, wherein the therapeutic or cosmetic active agent has a water solubility lower than 33 mg/mL and is loaded in a percentage of 0.5-5% by weight with respect to the total weight of the nonwoven membrane. In another particular embodiment, the nonwoven membrane of the invention comprises one single type of biocompatible electrospun nanofibers and microparticles of at least one therapeutic or cosmetic active agent in pure form entangled between the nanofibers, wherein one of the therapeutic or cosmetic active agents is SN-38 and is loaded in a percentage of 0.5-5% by weight with respect to the total weight of the nonwoven membrane. In a preferred embodiment, the nonwoven membrane of the invention comprises biocompatible electrospun nanofibers made of PLA and microparticles of at least one therapeutic or cosmetic active agent in pure form entangled between the nanofibers, wherein one of the therapeutic or cosmetic active agents is SN-38 and is loaded in a percentage of 0.5-5% by weight with respect to the total weight of the nonwoven membrane.

In a particular embodiment, the nonwoven membrane of the invention comprises biocompatible electrospun nanofibers made of PLA and microparticles of at least one therapeutic or cosmetic active agent in pure form entangled between the nanofibers, wherein the therapeutic or cosmetic active agent has a water solubility lower than 33 mg/mL and is loaded in a percentage of 0.75% by weight with respect to the total weight of the nonwoven membrane. In another particular embodiment, the nonwoven membrane of the invention comprises one single type biocompatible electrospun nanofibers and microparticles of at least one therapeutic or cosmetic active agent in pure form entangled between the nanofibers, wherein one of the therapeutic or cosmetic active agents is SN-38 and is loaded in a percentage of 0.75% by weight with respect to the total weight of the nonwoven membrane. In a preferred embodiment, the nonwoven membrane of the invention comprises biocompatible electrospun nanofibers made of PLA and microparticles of at least one therapeutic or cosmetic active agent in pure form entangled between the nanofibers, wherein one of the therapeutic or cosmetic active agents is SN-38 and is loaded in a percentage of 0.75% by weight with respect to the total weight of the nonwoven membrane.

In a particular embodiment, the nonwoven membrane of the invention comprises biocompatible electrospun nanofibers made of PLA and microparticles of at least one therapeutic or cosmetic active agent in pure form entangled between the nanofibers, wherein the therapeutic or cosmetic active agent has a water solubility lower than 33 mg/mL and the microparticles of the at least one therapeutic or cosmetic active agent have a mean diameter of 0.1-20 µm. In another particular embodiment, the nonwoven membrane of the invention comprises one single type of biocompatible electrospun nanofibers and microparticles of at least one therapeutic or cosmetic active agent in pure form entangled between the nanofibers, wherein one of the therapeutic or cosmetic active agents is SN-38 and the microparticles of the at least one therapeutic or cosmetic active agent have a mean diameter of 0.1-20 µm. In a preferred embodiment, the nonwoven membrane of the invention comprises biocompatible electrospun nanofibers made of PLA and microparticles of at least one therapeutic or cosmetic active agent in pure form entangled between the nanofibers, wherein one of the therapeutic or cosmetic active agents is SN-38 and the microparticles of the at least one therapeutic or cosmetic active agent have a mean diameter of 0.1-20 µm.

In a particular embodiment, the nonwoven membrane of the invention comprises biocompatible electrospun nanofibers made of PLA and microparticles of at least one therapeutic or cosmetic active agent in pure form entangled between the nanofibers, wherein the therapeutic or cosmetic active agent has a water solubility lower than 33 mg/mL and the microparticles of the at least one active agent have a mean diameter of 3-10 µm. In another particular embodiment, the nonwoven membrane of the invention comprises one single type of biocompatible electrospun nanofibers and microparticles of at least one therapeutic or cosmetic active agent in pure form entangled between the nanofibers, wherein one of the therapeutic or cosmetic active agents is SN-38 and the microparticles of the at least one therapeutic or cosmetic active agent have a mean diameter of 3-10 µm. In a preferred embodiment, the nonwoven membrane of the invention comprises biocompatible electrospun nanofibers made of PLA and microparticles of at least one therapeutic or cosmetic active agent in pure form entangled between the nanofibers, wherein one of the therapeutic or cosmetic active agents is SN-38 and the microparticles of the at least one therapeutic or cosmetic active agent have a mean diameter of 3-10 µm.

In a particular embodiment, the nonwoven membrane of the invention comprises biocompatible electrospun nanofibers made of PLA and microparticles of at least one therapeutic or cosmetic active agent in pure form entangled between the nanofibers, wherein the therapeutic or cosmetic active agent has a water solubility lower than 33 mg/mL and the microparticles of the at least one therapeutic or cosmetic active agent have a mean diameter of 0.5-5 µm. In another particular embodiment, the nonwoven membrane of the invention comprises one single type of biocompatible electrospun nanofibers and microparticles of at least one therapeutic or cosmetic active agent in pure form entangled between the nanofibers, wherein one of the therapeutic or cosmetic active agents is SN-38 and the microparticles of the at least one therapeutic or cosmetic active agent have a mean diameter of 0.5-5 µm. In a preferred embodiment, the nonwoven membrane of the invention comprises biocompatible electrospun nanofibers made of PLA and microparticles of at least one therapeutic or cosmetic active agent in pure form entangled between the nanofibers, wherein one of the therapeutic or cosmetic active agents is SN-38 and the microparticles of the at least one therapeutic or cosmetic active agent have a mean diameter of 0.5-5 µm.

The electrospun fibers of the invention have a diameter in the order of magnitude of some nanometers forming a membrane with large specific area. In a particular embodiment of the nonwoven membrane of the invention, the biocompatible electrospun nanofibers have a mean diameter of 50-1000 nm. In a preferred embodiment of the nonwoven membrane of the invention, the biocompatible electrospun nanofibers have a mean diameter of 200-600 nm. In another preferred embodiment of the nonwoven membrane of the invention, the biocompatible electrospun nanofibers have a mean diameter of 400-1000 nm.

In a particular embodiment, the nonwoven membrane of the invention comprises biocompatible electrospun nanofibers made of PLA and microparticles of at least one therapeutic or cosmetic active agent in pure form entangled between the nanofibers, wherein the therapeutic or cosmetic active agent has a water solubility lower than 33 mg/mL and the biocompatible electrospun nanofibers have a mean diameter of 50-1000 nm. In another particular embodiment, the nonwoven membrane of the invention comprises one single type of biocompatible electrospun nanofibers and microparticles of at least one therapeutic or cosmetic active agent in pure form entangled between the nanofibers, wherein one of the therapeutic or cosmetic active agents is SN-38 and the biocompatible electrospun nanofibers have a mean diameter of 50-1000 nm. In a preferred embodiment, the nonwoven membrane of the invention comprises biocompatible electrospun nanofibers made of PLA and microparticles of at least one therapeutic or cosmetic active agent in pure form entangled between the nanofibers, wherein one of the therapeutic or cosmetic active agents is SN-38 and the biocompatible electrospun nanofibers have a mean diameter of 50-1000 nm.

In a particular embodiment, the nonwoven membrane of the invention comprises biocompatible electrospun nanofibers made of PLA and microparticles of at least one therapeutic or cosmetic active agent in pure form entangled between the nanofibers, wherein the therapeutic or cosmetic active agent has a water solubility lower than 33 mg/mL and the biocompatible electrospun nanofibers have a mean diameter of 200-600 nm. In another particular embodiment, the nonwoven membrane of the invention comprises one single type of biocompatible electrospun nanofibers and microparticles of at least one therapeutic or cosmetic active agent in pure form entangled between the nanofibers, wherein one of the therapeutic or cosmetic active agents is SN-38 and the one biocompatible electrospun nanofibers have a mean diameter of 200-600 nm. In a preferred embodiment, the nonwoven membrane of the invention comprises biocompatible electrospun nanofibers made of PLA and microparticles of at least one therapeutic or cosmetic active agent in pure form entangled between the nanofibers, wherein one of the therapeutic or cosmetic active agents is SN-38 and the biocompatible electrospun nanofibers have a mean diameter of 200-600 nm.

In a particular embodiment, the nonwoven membrane of the invention comprises biocompatible electrospun nanofibers made of PLA and microparticles of at least one therapeutic or cosmetic active agent in pure form entangled between the nanofibers, wherein the therapeutic or cosmetic active agent has a water solubility lower than 33 mg/mL and the biocompatible electrospun nanofibers have a mean diameter of 400-1000 nm. In another particular embodiment, the nonwoven membrane of the invention comprises on single type of biocompatible electrospun nanofibers and microparticles of at least one therapeutic or cosmetic active agent in pure form entangled between the nanofibers, wherein one of the therapeutic or cosmetic active agents is SN-38 and the biocompatible electrospun nanofibers have a mean diameter of 400-1000 nm. In a preferred embodiment, the nonwoven membrane of the invention comprises biocompatible electrospun nanofibers made of PLA and microparticles of at least one therapeutic or cosmetic active agent in pure form entangled between the nanofibers, wherein one of the therapeutic or cosmetic active agents is SN-38 and the biocompatible electrospun nanofibers have a mean diameter of 400-1000 nm.

In a particular embodiment of the nonwoven membrane of the invention, the biocompatible electrospun nanofibers have a mean diameter of 50-1000 nm and the microparticles of the at least one therapeutic or cosmetic active agent have a mean diameter of 0.1-20 µm. In a preferred embodiment of the nonwoven membrane of the invention, the biocompatible electrospun nanofibers have a mean diameter of 50-1000 nm and the microparticles have a mean diameter of 3-10 µm. In another preferred embodiment of the nonwoven membrane of the invention, the biocompatible electrospun nanofibers have a mean diameter of 50-1000 nm and the microparticles have a mean diameter of 0.5-5 µm.

In a particular embodiment of the nonwoven membrane of the invention, the biocompatible electrospun nanofibers have a mean diameter of 200-600 nm and the microparticles of the at least one therapeutic or cosmetic active agent have a mean diameter of 0.1-20 µm. In a particular embodiment of the nonwoven membrane of the invention, the biocompatible electrospun nanofibers have a mean diameter of 200-600 nm and the microparticles of the at least one therapeutic or cosmetic active agent have a mean diameter of 3-10 μm. In a particular embodiment of the nonwoven membrane of the invention, the biocompatible electrospun nanofibers have a mean diameter of 200-600 nm and the microparticles of the at least one therapeutic or cosmetic active agent have a mean diameter of 0.5-5 μm.

In another particular embodiment, the biocompatible electrospun nanofibers have a mean diameter of 400-1000 nm and the microparticles of the at least one therapeutic or cosmetic active agent have a mean diameter of 0.1-20 μm. In another particular embodiment, the biocompatible electrospun nanofibers have a mean diameter of 400-1000 nm and the microparticles of the at least one therapeutic or cosmetic active agent have a mean diameter of 3-10 μm. In another particular embodiment, the biocompatible electrospun nanofibers have a mean diameter of 400-1000 nm and the microparticles of the at least one therapeutic or cosmetic active agent have a mean diameter of 0.5-5 μm.

In a particular embodiment, the nonwoven membrane of the invention comprises biocompatible electrospun nanofibers made of PLA and microparticles of at least one therapeutic or cosmetic active agent in pure form entangled between the nanofibers, wherein the therapeutic or cosmetic active agent has a water solubility lower than 33 mg/mL, the microparticles of the at least one therapeutic or cosmetic active agent have a mean diameter of 0.1-20 μm and the biocompatible electrospun nanofibers have a mean diameter of 50-1000 nm. In another particular embodiment, the nonwoven membrane of the invention comprises one single type of biocompatible electrospun nanofibers and microparticles of at least one therapeutic or cosmetic active agent in pure form entangled between the nanofibers, wherein the therapeutic or cosmetic active agent has a water solubility lower than 33 mg/mL, the microparticles of the at least one therapeutic or cosmetic active agent have a mean diameter of 0.1-20 μm and the biocompatible electrospun nanofibers have a mean diameter of 50-1000 nm. In a preferred embodiment, the nonwoven membrane of the invention comprises biocompatible electrospun nanofibers made of PLA and microparticles of at least one therapeutic or cosmetic active agent in pure form entangled between the nanofibers, wherein the therapeutic or cosmetic active agent has a water solubility lower than 33 mg/mL, the microparticles of the at least one therapeutic or cosmetic active agent have a mean diameter of 0.1-20 μm and the biocompatible electrospun nanofibers have a mean diameter of 50-1000 nm.

In a particular embodiment, the nonwoven membrane of the invention comprises biocompatible electrospun nanofibers made of PLA and microparticles of at least one therapeutic or cosmetic active agent in pure form entangled between the nanofibers, wherein the therapeutic or cosmetic active agent has a water solubility lower than 33 mg/mL, the microparticles of the at least therapeutic or cosmetic one active agent have a mean diameter of 3-10 μm and the biocompatible electrospun nanofibers have a mean diameter of 50-1000 nm. In another particular embodiment, the nonwoven membrane of the invention comprises one single type of biocompatible electrospun nanofibers and microparticles of at least therapeutic or cosmetic one active agent in pure form entangled between the nanofibers, wherein the therapeutic or cosmetic active agent has a water solubility lower than 33 mg/mL, the microparticles of the at least one therapeutic or cosmetic active agent have a mean diameter of 3-10 μm and the biocompatible electrospun nanofibers have a mean diameter of 50-1000 nm. In a preferred embodiment, the nonwoven membrane of the invention comprises biocompatible electrospun nanofibers made of PLA and microparticles of at least one therapeutic or cosmetic active agent in pure form entangled between the nanofibers, wherein the therapeutic or cosmetic active agent has a water solubility lower than 33 mg/mL, the microparticles of the at least one therapeutic or cosmetic active agent have a mean diameter of 3-10 μm and the biocompatible electrospun nanofibers have a mean diameter of 50-1000 nm.

In a particular embodiment, the nonwoven membrane of the invention comprises biocompatible electrospun nanofibers made of PLA and microparticles of at least one therapeutic or cosmetic active agent in pure form entangled between the nanofibers, wherein the therapeutic or cosmetic active agent has a water solubility lower than 33 mg/mL, the microparticles of the at least one therapeutic or cosmetic active agent have a mean diameter of 0.5-5 μm and the biocompatible electrospun nanofibers have a mean diameter of 50-1000 nm. In another particular embodiment, the nonwoven membrane of the invention comprises one single type of biocompatible electrospun nanofibers and microparticles of at least one therapeutic or cosmetic active agent in pure form entangled between the nanofibers, wherein the therapeutic or cosmetic active agent has a water solubility lower than 33 mg/mL, the microparticles of the at least one therapeutic or cosmetic active agent have a mean diameter of 0.5-5 μm and the biocompatible electrospun nanofibers have a mean diameter of 50-1000 nm. In a preferred embodiment, the nonwoven membrane of the invention comprises biocompatible electrospun nanofibers made of PLA and microparticles of at least one therapeutic or cosmetic active agent in pure form entangled between the nanofibers, wherein the therapeutic or cosmetic active agent has a water solubility lower than 33 mg/mL, the microparticles of the at least one therapeutic or cosmetic active agent have a mean diameter of 0.5-5 μm and the biocompatible electrospun nanofibers have a mean diameter of 50-1000 nm.

In a particular embodiment, the nonwoven membrane of the invention comprises biocompatible electrospun nanofibers made of PLA and microparticles of at least one therapeutic or cosmetic active agent in pure form entangled between the nanofibers, wherein the therapeutic or cosmetic active agent has a water solubility lower than 33 mg/mL, the microparticles of the at least one therapeutic or cosmetic active agent have a mean diameter of 0.1-20 μm and the biocompatible electrospun nanofibers have a mean diameter of 200-600 nm. In another particular embodiment, the nonwoven membrane of the invention comprises one single type of biocompatible electrospun nanofibers and microparticles of at least one therapeutic or cosmetic active agent in pure form entangled between the nanofibers, wherein the therapeutic or cosmetic active agent has a water solubility lower than 33 mg/mL, the microparticles of the at least one therapeutic or cosmetic active agent have a mean diameter of 0.1-20 μm and the biocompatible electrospun nanofibers have a mean diameter of 200-600 nm. In a preferred embodiment, the nonwoven membrane of the invention comprises biocompatible electrospun nanofibers made of PLA and microparticles of at least one therapeutic or cosmetic active agent in pure form entangled between the nanofibers, wherein the therapeutic or cosmetic active agent has a water solubility lower than 33 mg/mL, the microparticles of the at least one therapeutic or cosmetic active agent have a mean diameter of 0.1-20 μm and the biocompatible electrospun nanofibers have a mean diameter of 200-600 nm.

In a particular embodiment, the nonwoven membrane of the invention comprises biocompatible electrospun nanofibers made of PLA and microparticles of at least one therapeutic or cosmetic active agent in pure form entangled between the nanofibers, wherein the therapeutic or cosmetic active agent has a water solubility lower than 33 mg/mL, the microparticles of the at least one therapeutic or cosmetic active agent have a mean diameter of 3-10 μm and the biocompatible electrospun nanofibers have a mean diameter of 200-600 nm. In another particular embodiment, the nonwoven membrane of the invention comprises on single type of biocompatible electrospun nanofibers and microparticles of at least one therapeutic or cosmetic active agent in pure form entangled between the nanofibers, wherein the therapeutic or cosmetic active agent has a water solubility lower than 33 mg/mL, the microparticles of the at least one therapeutic or cosmetic active agent have a mean diameter of 3-10 μm and the biocompatible electrospun nanofibers have a mean diameter of 200-600 nm. In a preferred embodiment, the nonwoven membrane of the invention comprises biocompatible electrospun nanofibers made of PLA and microparticles of at least one therapeutic or cosmetic active agent in pure form entangled between the nanofibers, wherein the therapeutic or cosmetic active agent has a water solubility lower than 33 mg/mL, the microparticles of the at least one therapeutic or cosmetic active agent have a mean diameter of 3-10 μm and the biocompatible electrospun nanofibers have a mean diameter of 200-600 nm.

In a particular embodiment, the nonwoven membrane of the invention comprises biocompatible electrospun nanofibers made of PLA and microparticles of at least one therapeutic or cosmetic active agent in pure form entangled between the nanofibers, wherein the therapeutic or cosmetic active agent has a water solubility lower than 33 mg/mL, the microparticles of the at least one therapeutic or cosmetic active agent have a mean diameter of 0.5-5 μm and the biocompatible electrospun nanofibers have a mean diameter of 200-600 nm. In another particular embodiment, the nonwoven membrane of the invention comprises one single type of biocompatible electrospun nanofibers and microparticles of at least one therapeutic or cosmetic active agent in pure form entangled between the nanofibers, wherein the therapeutic or cosmetic active agent has a water solubility lower than 33 mg/mL, the microparticles of the at least one therapeutic or cosmetic active agent have a mean diameter of 0.5-5 μm and the biocompatible electrospun nanofibers have a mean diameter of 200-600 nm. In a preferred embodiment, the nonwoven membrane of the invention comprises biocompatible electrospun nanofibers made of PLA and microparticles of at least one therapeutic or cosmetic active agent in pure form entangled between the nanofibers, wherein the therapeutic or cosmetic active agent has a water solubility lower than 33 mg/mL, the microparticles of the at least one therapeutic or cosmetic active agent have a mean diameter of 0.5-5 μm and the biocompatible electrospun nanofibers have a mean diameter of 200-600 nm.

In a particular embodiment, the nonwoven membrane of the invention comprises biocompatible electrospun nanofibers made of PLA and microparticles of at least one therapeutic or cosmetic active agent in pure form entangled between the nanofibers, wherein the therapeutic or cosmetic active agent has a water solubility lower than 33 mg/mL, the microparticles of the at least one therapeutic or cosmetic active agent have a mean diameter of 0.1-20 μm and the biocompatible electrospun nanofibers have a mean diameter of 400-1000 nm. In another particular embodiment, the nonwoven membrane of the invention comprises one single type of biocompatible electrospun nanofibers and microparticles of at least one therapeutic or cosmetic active agent in pure form entangled between the nanofibers, wherein the therapeutic or cosmetic active agent has a water solubility lower than 33 mg/mL, the microparticles of the at least one therapeutic or cosmetic active agent have a mean diameter of 0.1-20 μm and the biocompatible electrospun nanofibers have a mean diameter of 400-1000 nm. In a preferred embodiment, the nonwoven membrane of the invention comprises biocompatible electrospun nanofibers made of PLA and microparticles of at least one therapeutic or cosmetic active agent in pure form entangled between the nanofibers, wherein the therapeutic or cosmetic active agent has a water solubility lower than 33 mg/mL, the microparticles of the at least one therapeutic or cosmetic active agent have a mean diameter of 0.1-20 μm and the biocompatible electrospun nanofibers have a mean diameter of 400-1000 nm.

In a particular embodiment, the nonwoven membrane of the invention comprises biocompatible electrospun nanofibers made of PLA and microparticles of at least one therapeutic or cosmetic active agent in pure form entangled between the nanofibers, wherein the therapeutic or cosmetic active agent has a water solubility lower than 33 mg/mL, the microparticles of the at least one therapeutic or cosmetic active agent have a mean diameter of 3-10 μm and the biocompatible electrospun nanofibers have a mean diameter of 400-1000 nm. In another particular embodiment, the nonwoven membrane of the invention comprises one single type of biocompatible electrospun nanofibers and microparticles of at least one therapeutic or cosmetic active agent in pure form entangled between the nanofibers, wherein the therapeutic or cosmetic active agent has a water solubility lower than 33 mg/mL, the microparticles of the at least one therapeutic or cosmetic active agent have a mean diameter of 3-10 μm and the biocompatible electrospun nanofibers have a mean diameter of 400-1000 nm. In a preferred embodiment, the nonwoven membrane of the invention comprises biocompatible electrospun nanofibers made of PLA and microparticles of at least one therapeutic or cosmetic active agent in pure form entangled between the nanofibers, wherein the therapeutic or cosmetic active agent has a water solubility lower than 33 mg/mL, the microparticles of the at least one therapeutic or cosmetic active agent have a mean diameter of 3-10 μm and the biocompatible electrospun nanofibers have a mean diameter of 400-1000 nm.

In a particular embodiment, the nonwoven membrane of the invention comprises biocompatible electrospun nanofibers made of PLA and microparticles of at least one therapeutic or cosmetic active agent in pure form entangled between the nanofibers, wherein the therapeutic or cosmetic active agent has a water solubility lower than 33 mg/mL, the microparticles of the at least one therapeutic or cosmetic active agent have a mean diameter of 0.5-5 μm and the biocompatible electrospun nanofibers have a mean diameter of 400-1000 nm. In another particular embodiment, the nonwoven membrane of the invention comprises one single type of biocompatible electrospun nanofibers and microparticles of at least one therapeutic or cosmetic active agent in pure form entangled between the nanofibers, wherein the therapeutic or cosmetic active agent has a water solubility lower than 33 mg/mL, the microparticles of the at least one therapeutic or cosmetic active agent have a mean diameter of 0.5-5 μm and the biocompatible electrospun nanofibers have a mean diameter of 400-1000 nm. In a preferred embodiment, the nonwoven membrane of the invention comprises biocompatible electrospun nanofibers made of PLA and microparticles of at least one therapeutic or cosmetic active agent in pure form entangled between the nanofibers, wherein the therapeutic or cosmetic active agent has a water solubility lower than 33 mg/mL, the microparticles of the at least one therapeutic or cosmetic active agent have a mean diameter of 0.5-5 µm and the biocompatible electrospun nanofibers have a mean diameter of 400-1000 nm.

The properties of nonwoven membranes of the invention (softness, lightness, malleability and endurance) make them appropriate to customize taylor-made suits to cover specific areas of a solid tissue (a tumor, for example) to be treated.

Therefore, in another aspect the invention provides a taylor-made suit comprising the nonwoven membrane as previously defined to cover a specific area of a solid tissue (thereafter "the taylor-made suit of the invention").

The taylor-made suit of the invention comprising the nonwoven membrane of the invention can be obtained, for example, according to the following method: first, a tridimensional image of the tissue/organ will be obtained through conventional imaging techniques (e.g. by ultrasound or by magnetic-resonance imaging). Then, the nonwoven membrane of the invention will be accordingly cut to wrap the surface of the treated tissue/organ.

Additionally, in another aspect the invention provides a method for obtaining the nonwoven membrane previously defined (thereafter "the method of the invention") that comprises the steps of:
  (a) electrospinning a solution of one single type of a biocompatible polymer; and
  (b) simultaneously pouring on top of the collector a suspension of microparticles of at least one therapeutic or cosmetic active agent for obtaining an electrospun nonwoven membrane comprising biocompatible electrospun nanofibers and microparticles of at least one therapeutic or cosmetic active agent entangled between said nanofibers.

The solution of the biocompatible polymer of step (a) can be a solution of the polymer solved in a proper solvent or alternatively the polymer melted, and can be prepared by any appropriate method of the art.

The choice of a proper solvent for the process was a very important parameter studied, because it determines whether fibers are capable of forming, as well as influences fiber porosity. In order for sufficient solvent evaporation to occur between the capillary tip and the collector a volatile solvent must be used. As the fiber jet travels through the atmosphere toward the collector a phase separation occurs before the solid polymer fibers are deposited, a process that is greatly influenced by the volatility of the solvent.

The most suitable solvents for dissolving PLA, for example, found during the research were dichloromethane and chloroform, because they are very potent solvents and allowed electrospinning process. However, the use of chloroform as solvent was discarded due to its toxicity and related manipulation complexity during the electrospinning process. Other possible solvents to be used in the method of the invention can be ethyl acetate, acetone, dimethylformamide and dimethylsulfoxyde (DMSO). In any case, the skilled person will select the solvent according to the nature of polymer to be solved.

The solvent chosen to carry out the research was dichloromethane, because it is considered the least toxic of the simple organochloride compounds. However, this solvent presents some health risks as its high volatility makes it an acute inhalation hazard. In order to avoid the solvent inhaling risk, the electrospinning device should be provided with an air extractor.

In a particular embodiment of the method of the invention, the solution of the biocompatible polymer of step (a) is a solution of PLA in dichloromethane.

After selecting a suitable solvent, it was necessary to establish the best polymer concentration, since it determines the spinnability of a solution, namely whether a fiber forms or not. The polymer concentration influences both the viscosity and the surface tension of the solution, both of which are very important parameters in the electrospinning process.

In the method of the invention, the best conditions were provided by a polymer concentration of 10% of the solution weight. High concentration solutions, over 10%, increased enormously solution viscosity, which made it difficult to control the solution flow rate through the capillary and, consequently, the electrospinning process. It was also noted in some experiments that the fiber diameter of obtained membranes could increase with increasing solution concentration. If the solution is too diluted, due to the decreasing effects on surface tension and viscosity, a secondary and simultaneous process occurs, namely electrospraying, in which the polymer fiber break up into droplets before reaching the collector.

In a particular embodiment of the method of the invention, the polymer concentration ranges from 8 to 15% of the solution weight. In a preferred embodiment of the method of the invention, the polymer concentration is 10% of the solution weight.

Once prepared the solution of biocompatible polymer, this is submitted to an electrospinning process (FIG. 1) in an electrospinning device that can be anyone of the art. For this purpose, the polymer solution is held by its surface tension at the end of a capillary tube and is subjected to an electric field. When the electric field applied reaches a critical value, the repulsive electrical forces overcome the surface tension forces. Eventually, a charged jet of the solution is ejected from the tip of the Taylor cone and an unstable and a rapid whipping of the jet occurs in the space between the capillary tip and collector which leads to evaporation of the solvent, leaving a polymer behind and leading to a mat of nanofibers deposited on the collector.

The high voltage tension applied to the jet was a critical value ranging from 8 kV to 20 kV, and the best applied voltage found to improve the process was 10 kV. At this voltage electrospinning process is carried out uniformly, with the Taylor's cone formation, without bead defects and production of regular polymeric fibers with diameters in nanoscale. Additional optimal configuration was found for spinning flow rate, distance from spinneret to collector, size, shape and nature of collector, room temperature and humidity and spinning chamber geometry.

The electrospinning was carried out for a time of 15-40 min, preferably a time of 20 min with a flow of polymer solution of 0.4-0.6 ml/h, preferably of 0.5 ml/h, depending on the diameter of the needle used.

The shape and dimensions of the nonwoven membrane so obtained will be assessed by the expert according to the final purpose of it.

In a particular embodiment of the method of the invention, the thickness of the nonwoven membrane ranges from 0.05 to 0.5 mm. In a preferred embodiment of the method of the invention, the thickness of the nonwoven membrane is of 0.2 mm.

During the electrospinning of the polymer solution the suspension of microparticles is simultaneously loaded within the membrane. The loading process can be carried out by any method that allows the entrapment of microparticles between the nanofibers. For example, a particular dose of microparticles in suspension can be loaded in a syringe attached to an infusion pump and poured on top of the collector at regular time intervals during the electrospinning process.

The suspension of microparticles of the at least one therapeutic or cosmetic active agent of step (b) can be prepared by different methods of the art as previously stated.

A suspension of therapeutic agent microcrystals can be prepared by the precipitation method, either by solvent incompatibility or pH-dependent crystallization, preferably by pH-dependent crystallization. Additionally, a suspension of active protein microparticles can be obtained by lyophilisation and further addition of an appropriate solvent.

In a particular embodiment of the method of the invention, the suspension of microparticles is prepared by lyophilisation of a solution of at least one therapeutic or cosmetic active agent followed by the addition of a solvent in which the agent is soluble at a concentration lower than 33 mg/mL.

In a particular embodiment of the method of the invention, the suspension of microparticles is prepared by precipitation. In a particular embodiment of the method of the invention, the suspension of microparticles is prepared by adding to the solution of at least one therapeutic or cosmetic active agent a solvent in which the therapeutic or cosmetic active agent is insoluble. In a preferred embodiment of the method of the invention, the suspension of microparticles is prepared by adding to the solution of at least one therapeutic or cosmetic active agent a solution having a pH at which the active agent is insoluble.

Optionally, a surfactant is used for stabilizing the suspension of microparticles. The surfactant can be added to the solution of at least one active agent before adding the solvent or the solution in which the therapeutic or cosmetic active agent is insoluble. Alternatively, the surfactant can be added to the solvent or the solution in which the therapeutic or cosmetic active agent is insoluble and then this mixture is added to the solution of at least one therapeutic or cosmetic active agent. Alternatively, the surfactant can be added both to the solution of at least one therapeutic or cosmetic active agent and to the solvent or the solution in which the therapeutic or cosmetic active agent is insoluble.

This surfactant can be a non-ionic surfactant approved by FDA or other regulatory agency such as a Pluronic surfactant (F68, F127 F108, L101, L121, P85, P105 or P123), a Tetronic surfactant (T1307, T1107 or T904), phosphatidylcholine, phosphatidylethanolamine, lecithin, polyvinyl alcohol, polyvinylpyrrolidone, or Tween 80 for example. The surfactant can be used at a concentration of 0.01-10%, preferably of 2% by weight of total volume of solution. In any case minimum amounts of the surfactant agent could remain in the microparticles of therapeutic or cosmetic active agent and could aid to dissolve it once the nonwoven membrane would be placed into the area to be treated.

In a particular embodiment of the method of the invention, the suspension of microparticles is prepared by mixing a solution of at least one therapeutic or cosmetic active agent with a solution comprising a surfactant and having a pH at which the therapeutic or cosmetic active agent is insoluble.

Optionally, the method of the invention can include a further step of drying the nonwoven membrane so obtained. In a particular embodiment of the method of the invention, the nonwoven membrane obtained in step (b) is dried at room temperature and under vacuum.

Optionally, the nonwoven membrane so obtained can be further coated on one side by one of the following methods: adhesion with biocompatible glue, contact with polymer solvent, mechanical punch, or electrospinning parameters that favor fiber adhesion. In a particular embodiment of the method of the invention, the nonwoven membrane obtained in step (b) is coated on one side. In a particular embodiment of the method of the invention, the nonwoven membrane obtained in step (b) is dried and then coated on one side.

In a particular embodiment of the method of the invention, it comprises the steps of:
  (i) at least electrospinning a solution of one single type of a biocompatible polymer for collecting a first layer of a nonwoven membrane comprising biocompatible electrospun nanofibers;
  (ii) at least electrospinning a solution of one single type of a biocompatible polymer and simultaneously pouring a suspension of microparticles of at least one therapeutic or cosmetic active agent for collecting over the first layer a second layer of a nonwoven web comprising biocompatible electrospun nanofibers and microparticles of at least one single type of active agent entangled between said nanofibers; and
  (iii) at least electrospinning a solution of a one single type of biocompatible polymer for collecting over the second layer a third layer of a nonwoven membrane comprising biocompatible electrospun nanofibers.

The parameters and conditions are similar to those previously disclosed.

The shape and dimensions of each layer of the nonwoven membrane so obtained will be assessed by the expert according to the final purpose of it.

In a particular embodiment of the method of the invention, the thickness of each layer of the nonwoven membrane ranges from 0.05 to 0.5 mm. In a preferred embodiment of the method of the invention, the thickness of each layer of the nonwoven membrane is of 0.2 mm.

In a preferred embodiment of the method of the invention, it comprises the steps of:
  (i) electrospinning one solution of one single type of a biocompatible polymer for collecting one first layer of a nonwoven membrane comprising biocompatible electrospun nanofibers;
  (ii) electrospinning one solution of one single type of a biocompatible polymer and simultaneously pouring a suspension of microparticles of at least one therapeutic or cosmetic active agent for collecting over the first layer one second layer of a nonwoven web comprising biocompatible electrospun nanofibers and microparticles of at least one therapeutic or cosmetic active agent entangled between said nanofibers; and
  (iii) electrospinning one solution of one single type of a biocompatible polymer for collecting over the second layer one third layer of a nonwoven membrane comprising biocompatible electrospun nanofibers.

In another preferred embodiment of the method of the invention, it comprises the steps of:
  (i) at least electrospinning a solution of one single type of a biocompatible polymer for collecting a first layer of a nonwoven membrane comprising biocompatible electrospun nanofibers;
  (ii) at least electrospinning a solution of one single type of a biocompatible polymer and simultaneously pouring a suspension of microparticles of at least one first therapeutic or cosmetic active agent for collecting over the first layer a previous second layer of a nonwoven web comprising biocompatible electrospun nanofibers and microparticles of at least one first therapeutic or cosmetic active agent entangled between said nanofibers;

(ii') at least electrospinning a solution of one single type of a biocompatible polymer and simultaneously pouring a suspension of microparticles of at least one second therapeutic or cosmetic active agent for collecting over the previous second layer a subsequent second layer of a nonwoven web comprising biocompatible electrospun nanofibers and microparticles of at least one second therapeutic or cosmetic active agent entangled between said nanofibers, and (iii) at least electrospinning a solution of one single type of a biocompatible polymer for collecting over the subsequent second layer a third layer of a nonwoven membrane comprising biocompatible electrospun nanofibers.

In a particular embodiment of the method of the invention, the nonwoven membrane obtained in step (iii) is dried at room temperature and under vacuum.

Optionally, the nonwoven membrane so obtained can be further coated on one side by one of the following methods: adhesion with biocompatible glue, contact with polymer solvent, mechanical punch, or electrospinning parameters that favor fiber adhesion. In a particular embodiment of the method of the invention, the nonwoven membrane obtained in step (iii) is coated on one side. In a particular embodiment of the method of the invention, the nonwoven membrane obtained in step (iii) is dried and then coated on one side. In a more particular embodiment of the method of the invention, the nonwoven membrane obtained in step (iii) is coated on the side of the first layer. In another more particular embodiment of the method of the invention, the nonwoven membrane obtained in step (iii) is coated on the side of the third layer. In a preferred embodiment of the method of the invention, the nonwoven membrane obtained in step (iii) is dried and then coated on the side of the first layer. In another preferred embodiment of the method of the invention, the nonwoven membrane obtained in step (iii) is dried and then coated on the side of the third layer.

In other aspect, the invention provides the use of the nonwoven membrane previously defined for the local delivery of an therapeutic or cosmetic active ingredient in a controlled and sustained manner to a body area to be treated.

In other aspect, the invention provides the use of the taylor-made suit previously defined to cover a specific area of a solid tissue selected from skin, mucosas, bones, muscles, internal organs and solid tumors.

In oncology, for example, the nonwoven membrane and/or the taylor-made suit of the invention are useful for treating tumors that include non-resectable areas with vital vessels, for treating surgical borders wherein tumor residues are left, or for treating osseous tissues with tumor infiltration or positive bone scan. They are also useful for tissue regeneration by treating the damaged tissues on which the regenerating factors are being released or for releasing antibiotics to a post-surgery area.

The nonwoven membrane of the invention can be applied by overlapping the surface to be treated and then suturing the membrane borders to the surrounding tissue.

The taylor-made suit comprising the nonwoven membrane of the invention can be applied by wrapping the surface of the tissue or organ to be treated.

Local delivery of drugs loaded in the nonwoven membrane of the invention renders high drug concentrations within the tumor bulk, reduces systemic drug exposure and is safe to surrounding healthy tissues.

The following examples illustrate the invention and should not be considered as limiting its scope of application Example 1

Preparation of a Nonwoven Membrane Comprising Electrospun PLA Nanofibers and SN-38 Microcrystals 1.1 Preparation of a Suspension of SN-38 Microcrystals.

Figure 2:
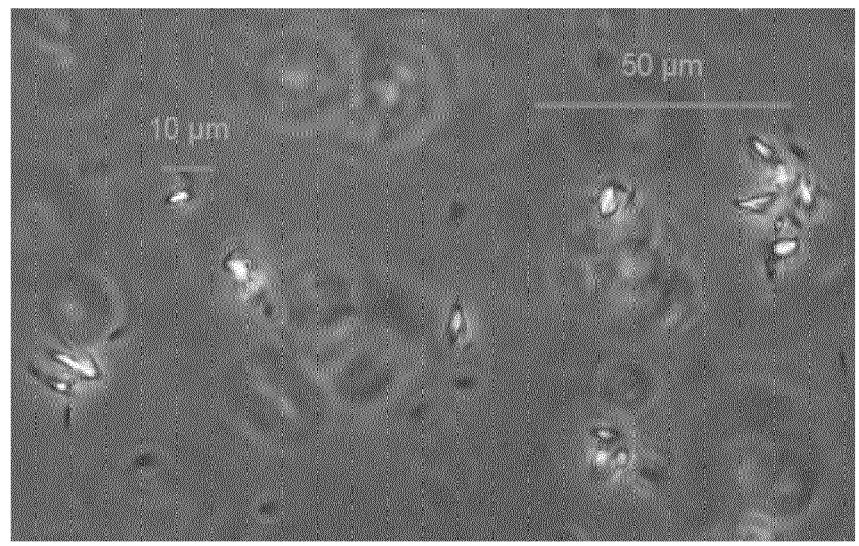
FIG. 2 shows an optical microscopy image of the suspension of SN-38 microcrystals to be used for obtaining the nonwoven membrane of the invention.

To a 50 mL pH 5.0 acetate buffer was added 2% Pluronic F68. Then SN-38 was dissolved (4 mg/mL) in NaOH 0.1 N, ratio 9:1. The acetate buffer (450 µL) was poured on the SN-38 solution (50 µL, in an eppendorf) with agitation at room temperature. No turbidity was observed during the first hour at room temperature. After 1 hour, small crystals appeared. Samples were stored at 4° C. for 24 h with hourly agitation. After that no aggregates were observed as the suspension was very stable. The mean diameter of the microcrystals in the suspension was determined by optical microscopy, being of 0.5-5 µm. FIG. 2 shows an optical microscopy image of the suspension of SN-38 microcrystals so prepared.

1.2 Preparation of a Nonwoven Membrane Comprising Electrospun PLA Nanofibers and SN-38 Microcrystals Entangled Between the PLA Nanofibers.

A nonwoven membrane was prepared having a first layer of electrospun PLA nanofibers, a second layer of electrospun PLA nanofibers and SN-38 microcrystals entangled between the PLA nanofibers and a third layer of electrospun PLA nanofibers.

Briefly, PLA was dissolved in methylene chloride in a concentration of 10% by weight, loaded in a syringe and introduced in a constant rate pump attached to the electrospinning machine.

Figure 3:
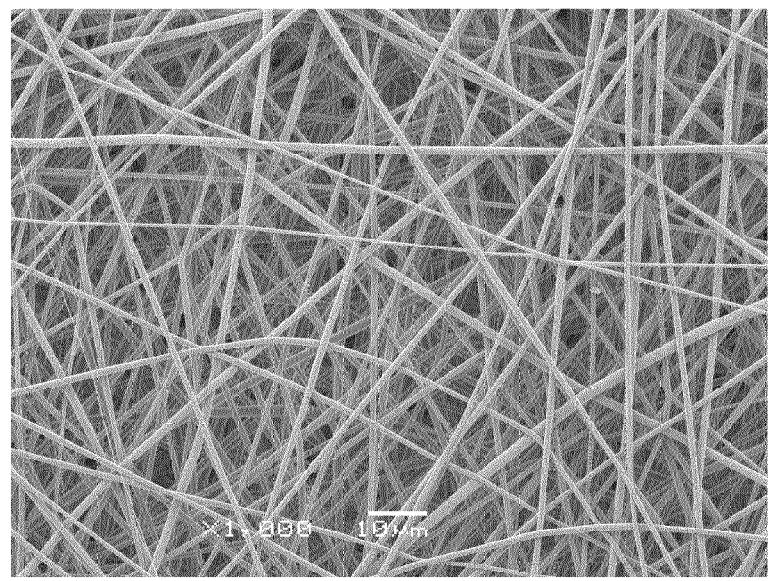
FIG. 3 shows a scanning electron micrograph of the nonwoven membrane of the invention having regular electrospun PLA nanofibers before to be loaded with SN-38 microcrystals.

17 mg of PLA were spinned (20 min with a flow of 0.5 ml/hour of PLA solution and at a voltage of 10 kV) to form a first layer of a PLA nonwoven membrane without drug over a substrate of vegetal paper, having 50 mm diameter and 0.2 mm thickness. This nonwoven membrane had regular PLA nanofibers as shown in FIG. 3. This first layer served as support for the upcoming drug-loaded layer.

Then, the suspension of microparticles prepared in 1.1 (1 mL containing 400 µg of crystallized SN-38) was divided in 20 fractions and each fraction was poured at time intervals of 1 minute during the process of electrospinning of additional 20 mg of PLA. A second layer was formed of a PLA nonwoven membrane loaded with drug and having 50 mm diameter and 0.2 mm thickness.

After loading the complete suspension of the drug microparticles, 17 mg of PLA were spinned (20 min with a flow of 0.5 ml/hour of PLA solution and at a voltage of 10 kV) to form a third layer of a PLA nonwoven membrane without drug and having 50 mm diameter and 0.2 mm thickness.

Figure 4:
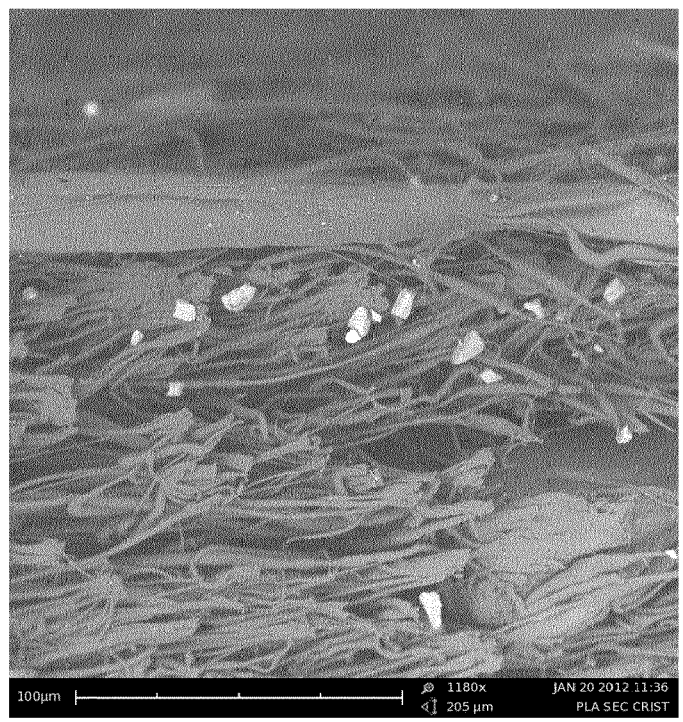
FIG. 4 shows a scanning electron micrograph of a transverse cut of a nonwoven membrane of the invention comprising electrospun PLA nanofibers and SN-38 microcrystals entangled between the PLA nanofibers (×1180).
Figure 5:
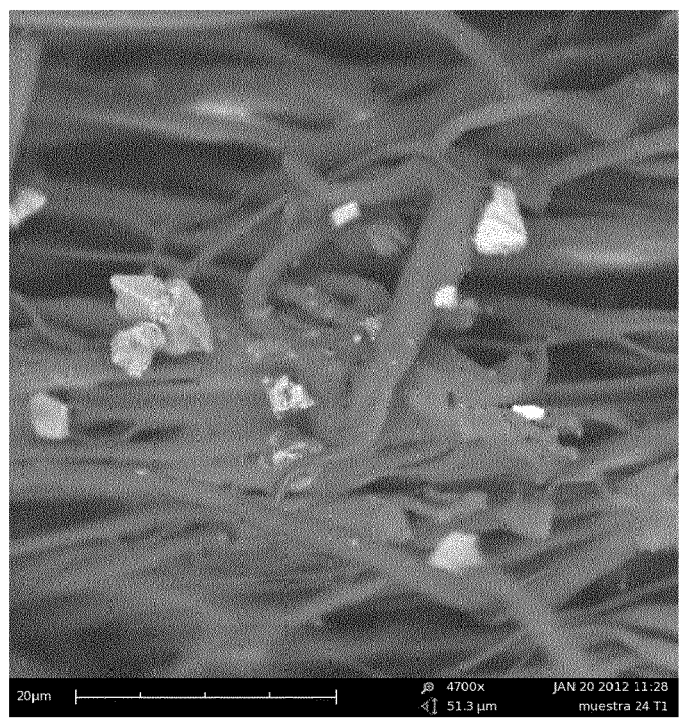
FIG. 5 shows a scanning electron micrograph of a transverse cut of a nonwoven membrane of the invention comprising electrospun PLA nanofibers and SN-38 microcrystals entangled between the PLA nanofibers (×4700).

Finally, the nonwoven membrane so prepared was dried at room temperature and under vacuum for 24 h. FIG. 4 and FIG. 5 are scanning electron micrographs of the nonwoven membrane obtained at different magnifications (×1180 and ×4700, respectively).

In the nonwoven membrane prepared, the PLA nanofibers had a mean diameter of 400-1000 nm, as determined by scanning electron microscopy, the SN-38 microcrystals had a mean diameter of 0.5-5 µm, and the theoretical amount of SN-38 loaded was 0.75% by weight (i.e., 0.4 mg of SN-38 loaded in a 54 mg membrane).

Example 2

In Vitro Characterization of the Nonwoven Membrane Obtained in Example 1

Assays were carried out in order to characterize the in vitro release pattern and the activity in vitro of the prepared membrane.

In Vitro Release Pattern

To study the release profile of the drug entrapped in the nonwoven membrane of the invention in vitro experiments were performed using 5 mm diameter membranes containing 5 µg of SN-38 crystals. Membranes were introduced in 24 well plates containing 400 µL of cell culture medium (RPMI) each, at 37° C. The complete volume was removed at established time points (8, 24, 48 and 96 hours) and renewed with fresh medium. Released drug was quantified with a high performance liquid chromatographer (Shimadzu) with a fluorescence detector. Drug released at each time point is represented in FIG. 6, and accumulated release is represented in FIG. 7.

Figure 6:
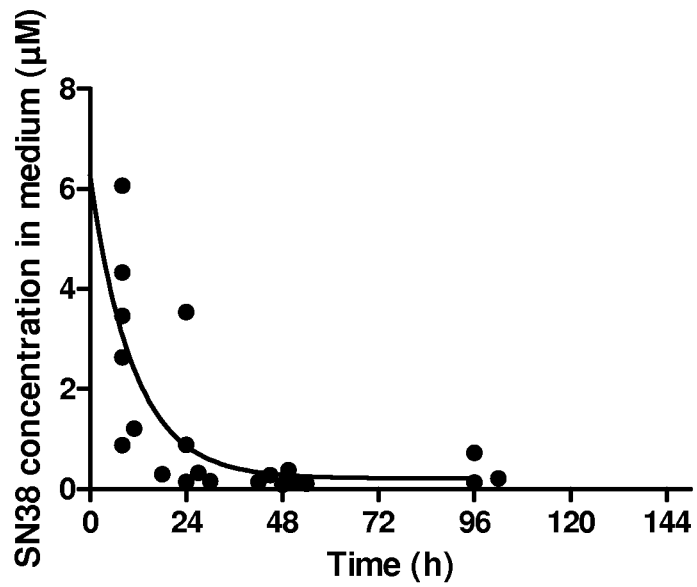
FIG. 6 shows the in vitro release profile of 5 mm diameter nonwoven membranes of the invention comprising electrospun PLA nanofibers and SN-38 microcrystals entangled between the PLA nanofibers.

FIG. 6 shows the in vitro release profile of the 5 mm diameter membranes prepared. Individual dots represent drug released by individual membranes and line represents the model fitting the release pattern.

Figure 7:
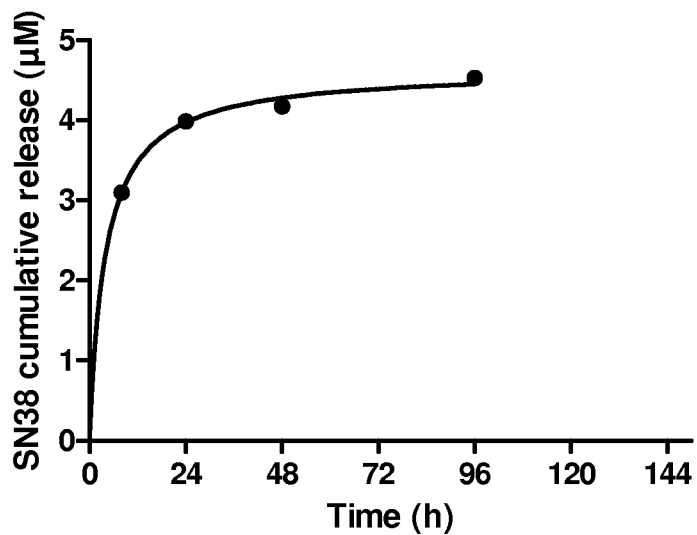
FIG. 7 shows the accumulated SN-38 release from 5 mm diameter nonwoven membranes of the invention comprising electrospun PLA nanofibers and SN-38 microcrystals entangled between the PLA nanofibers.

FIG. 7 shows the accumulated SN-38 release from the 5 mm diameter membranes prepared. Dots represent means and line the best-fitting curve.

Activity In Vitro

Experiment A

Conservation of Antitumor Activity of the Active Agent after Manufacturing the Nonwoven Membrane of the Invention To determine whether the antitumor activity of the drug was conserved after the manufacturing process of the membranes, the present inventors co-incubated the membranes with neuroblastoma cell lines. In a previous experiment, the present inventors determined the extent to which SN-38 inhibits neuroblastoma. Such experiment was performed by exposing LAN-1, SK-N-BE(2)c and SK-N-AS cell lines to a fresh solution of SN-38 in RPMI, prepared from a stock solution of SN-38, 1 mg/mL in DMSO. Briefly, cells were plated in 96 well plates, 3000 cells per well, in RPMI medium. 24 hours later, the cells were exposed to SN-38 (concentration range 10-0.000001 µM). After 4 hours, the drug was withdrawn and fresh medium was added. The viability of the cell culture was quantified 4 days later, by using the MTS cell viability assay (Promega). The established IC50 values were in the nanomolar range: 10 nM, 46 nM and 190 nM for LAN-1, SK-N-BE(2)c and SK-N-AS cells, respectively (FIG. 8).

Figure 8:
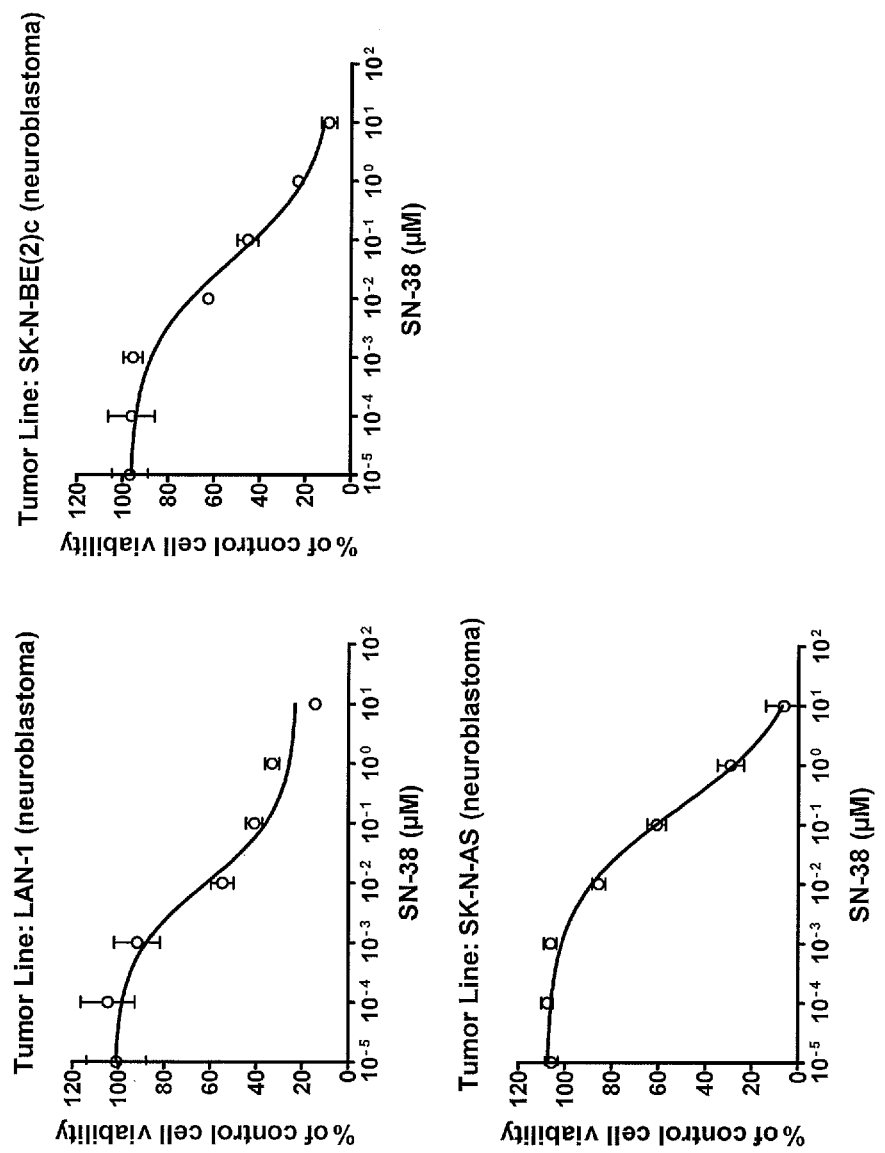
FIG. 8 shows the in vitro activity of a solution of soluble SN-38 (non loaded in the nonwoven membrane of the invention) on several neuroblastoma cell lines, expressed as the percentage of cell viability as compared to untreated, control wells.

FIG. 8 shows the in vitro activity of a fresh solution of soluble SN-38 against several neuroblastoma cell lines, expressed as the percentage of cell viability as compared to untreated, control wells. Each dot represents the mean (±SD) of 3-5 wells.

Figure 9:
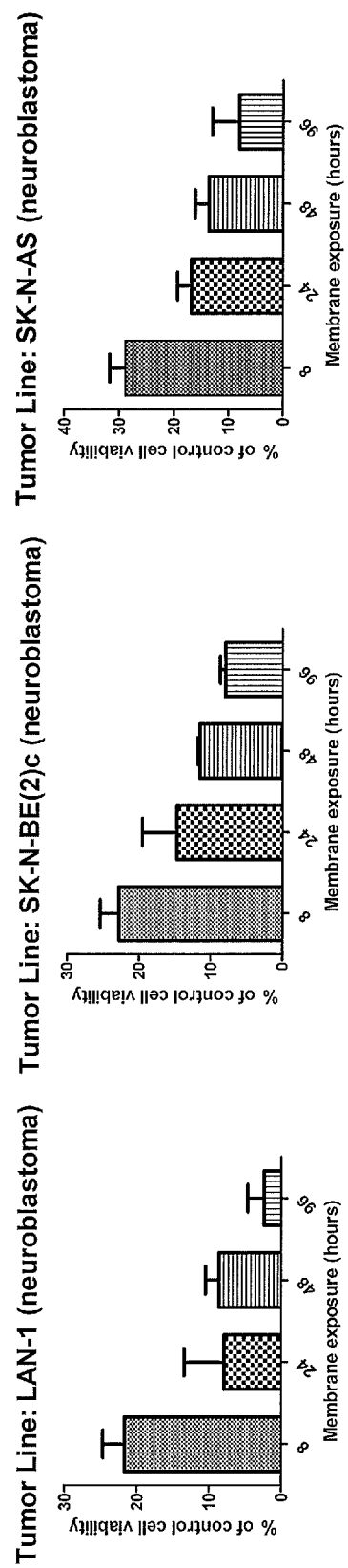
FIG. 9 shows the in vitro activity of the SN-38 microcrystals loaded in the nonwoven membrane of the invention on several neuroblastoma cell lines, expressed as the percentage of cell viability as compared to untreated, control cells.

To study the antitumor activity of the manufactured membrane, 5 mm diameter membranes loaded with 5 µg SN-38 microcrystals were co-incubated with cells in 24 well plates. Briefly, cells were plated, 12000 cells per well, and let 24 hours in the incubator. Then, one membrane was added to each well and withdrawn at predetermined time points (8, 24, 48 and 96 hours). At each time point, the cell culture medium was removed from all wells (including treated wells and control-untreated ones) and fresh medium was added. After 96 hours, the viability of the cultures was evaluated with the MTS assay. The present inventors observed that the membranes inhibited significantly the growth of the tumor cells, as a sign of the conserved activity of the drug (FIG. 9). The present inventors also observed that longer exposures to the membranes induced more potent antitumor activity, which suggested sustained drug release from the formulations.

FIG. 9 shows the in vitro activity of the SN-38 loaded nonwoven membranes on several neuroblastoma cell lines, expressed as the percentage of cell viability as compared to untreated, control cells. Means (±SD) of 3 wells were represented.

Experiment B

Sustained Release of the Active Agent from the Nonwoven Membrane of the Invention To verify the sustained release of active drug from the membranes, the present inventors designed an experiment in which membranes were pre-released in medium, previously to be transferred to cell cultures. Briefly, cells were plated as in experiment A and, in parallel, membranes were pre-released for 24 or 48 hours in 400 µL of fresh medium without cells at 37° C. Then, the membranes were transferred to the cell cultures, as in experiment A. After 3 days of incubation, the membranes were removed and the viability of the cells quantified with the MTS assay. The present inventors observed that pre-released membranes conserved a significant fraction of the activity as compared to intact membranes (control), suggesting that the formulation is active for prolonged time periods, at least 48 hours, and can be carried within the membrane (FIG. 10).

Figure 10:
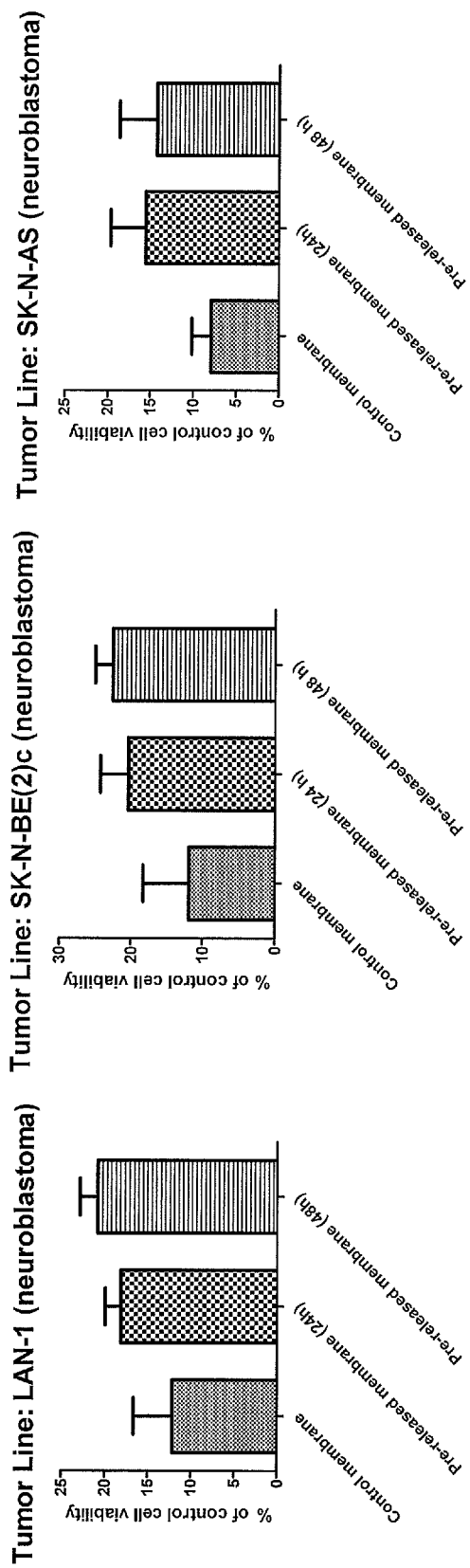
FIG. 10 shows the activity of the pre-released nonwoven membranes and intact nonwoven membranes (control) according to the invention, expressed as the percentage of cell viability as compared to untreated cells.

FIG. 10 shows the activity of the pre-released membranes and control (intact) membranes, expressed as the percentage of cell viability as compared to untreated cells. Means (±SD) of 3 wells are represented.

Experiment C

Evidence that the Cytotoxic Activity of the Pre-Released Membranes is Due to the Entrapped, Unreleased Active Agent To further verify that the cytotoxic activity of the pre-released membranes observed in Experiment B is due to the entrapped, unreleased drug and not to the absorption of previously released, soluble drug, or to the matrix by itself, the present inventors co-cultured empty (control membranes) with SN-38 loaded membranes for 24 hours in 24 well plates. In each well the present inventors co-incubated one loaded membrane and one empty membrane, in 400 µL of RPMI medium. Both co-incubated membranes were washed in 5 mL of fresh PBS and then transferred, one by one, to neuroblastoma cell cultures (plated as in experiments A and B). Cells were cultured 3 days with the membranes and the MTS assay was then performed. The results showed that the empty membranes were not cytotoxic, even after co-incubation with loaded ones, which ensured that the soluble drug is not carried absorbed by the empty membrane. As opposite, loaded membranes, either intact or pre-released for 24 hours during co-incubation with empty ones, conserved their expected activity, as already demonstrated in experiments A and B.

Figure 11:
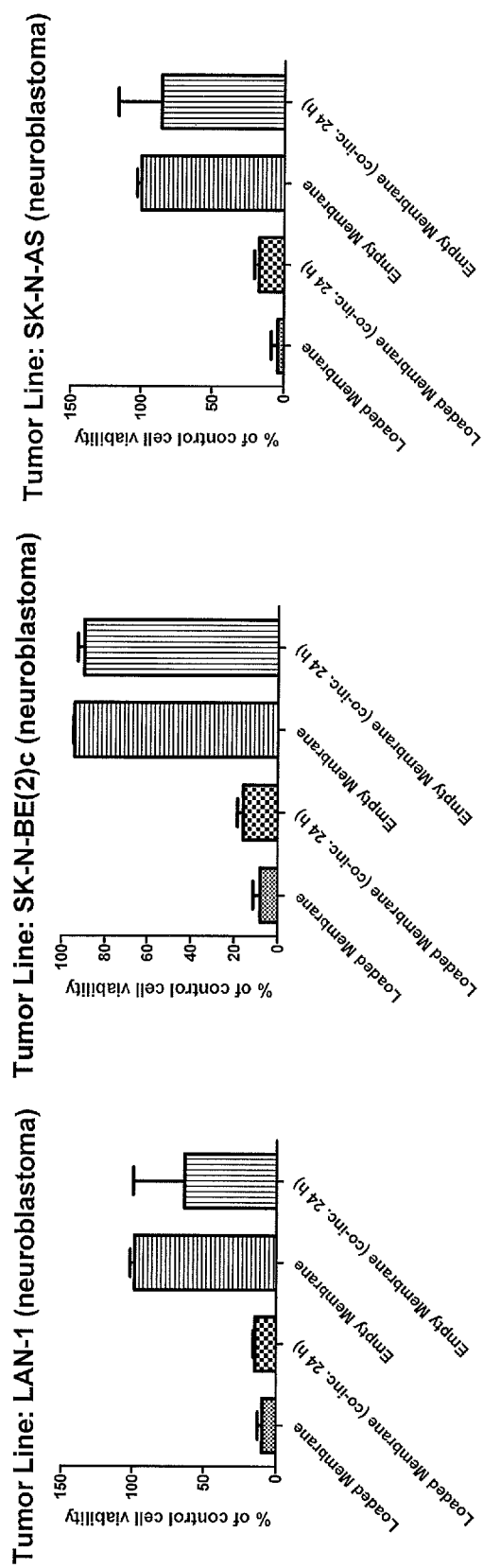
FIG. 11 shows the activity of the co-incubated nonwoven membranes (loaded and empty ones) and control nonwoven membranes (loaded and empty ones, not co-incubated) according to the invention, expressed as the percentage of cell viability as compared to untreated cells.

FIG. 11 shows the activity of the co-incubated nonwoven membranes (loaded and empty ones) and control nonwoven membranes (loaded and empty ones, not co-incubated), expressed as the percentage of cell viability as compared to untreated cells. Means (±SD) of 3 wells are represented.

Example 3

In Vivo Characterization of the Membrane Obtained in Example 1

Figure 12:
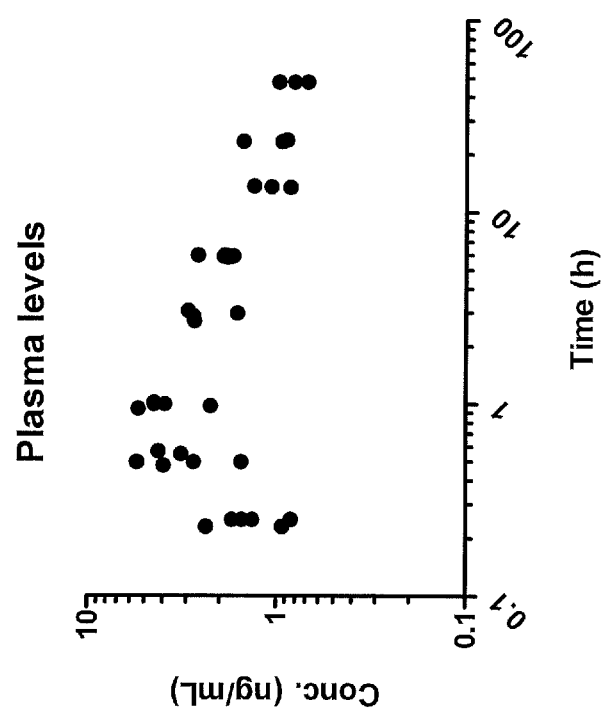
FIG. 12 shows the plasma pharmacokinetics of a single mm diameter membrane loaded with 100 μg SN-38 implanted subcutaneously in athymic mice.

Membranes were cut into 12 mm diameter circular pieces containing 100 µg SN-38 each. One membrane was inserted subcutaneously in CD1 nude mice (n=11; Charles River); i.e., each mouse (average weight 25 g/mouse) received a 4 mg/kg dose of SN-38. Blood samples (100 µL) were obtained from the retroorbital plexus at different time points during 48 hours and SN-38 levels were determined by high performance liquid chromatography. Results are shown in FIG. 12. Such results show SN-38 exposure in plasma is low and nontoxic during the local release of SN-38 from the membrane to the surrounding tissues, as previously hypothesized by the inventors. After the pharmacokinetic experiment mice were observed closely for adverse effects during the following days-weeks. Slight swelling was observed during the first days. After the resolution of the swelling, skin around the membrane remained slightly protruded until the end of the experiment (at least 12 weeks from the insertion of the membrane); as a result of a fraction of the PLA nanofibers remaining undegraded. This observation was expected due to long degradation half time of PLA. No weight loss of the mice was observed. Overall, the membrane appeared safe under the selected experimental conditions.

In Vivo Activity of the Membrane Obtained in Example 1.

Figure 13:
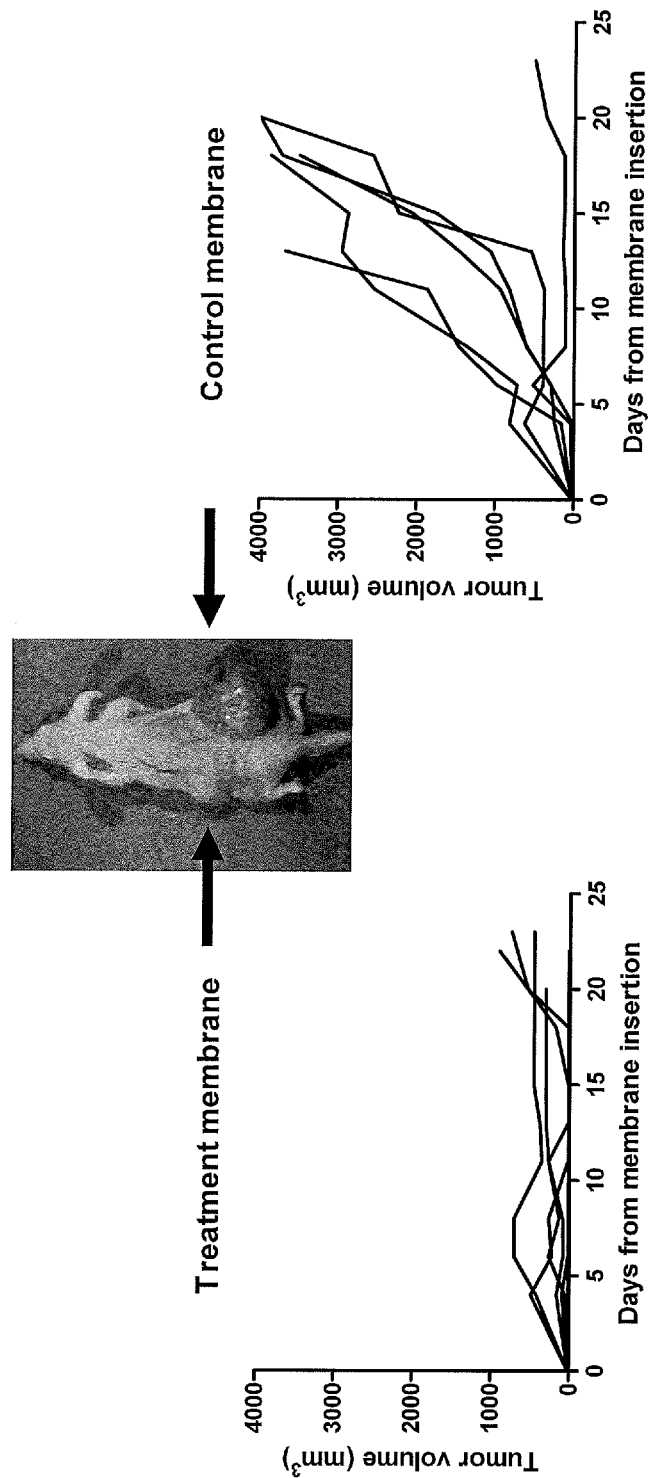
FIG. 13 shows the activity of the membranes loaded with 100 μg SN-38, as compared to control (blank) membranes, to inhibit growth of a subcutaneously implanted human tumor in athymic mice.

Six nude mice (Harlan) were subcutaneously implanted with small pieces (2 mm diameter) of aggressive human neuroblastoma tumors, one on each flank. Tumors grew during the next 27 days until reaching 1000-4000 mm³. On day 27, as a model of incomplete tumor resection, 95% of tumor volume was resected under complete anesthesia and a viable and vascularized tumor fraction (5% volume) was left in each flank. Then, 12 mm diameter membranes, either drug-free (control) or drug-loaded (containing 100 µg SN-38) were inserted subcutaneously on top of the right and left tumor rests, respectively, and wounds were closed with sutures. Mice recovered and tumor growth was measured with caliper during the following 23 days. Results in FIG. 13 show tumor growth inhibition achieved with locally implanted drug-loaded membranes, as compared to control membranes. Our experiment confirms that the activity of the DDS is due to the drug released locally and not to systemic drug exposure achieved from the DDS, because only tumors in contact with drug-loaded membranes responded to treatment.

The invention claimed is:

1. A nonwoven membrane comprising biocompatible electrospun nanofibers and microparticles of at least one therapeutic or cosmetic active agent in pure form, entangled between the nanofibers which are of one single type of polymer, characterized in that the therapeutic or cosmetic active agent has a water solubility lower than 33 mg/mL and it is released from the membrane after dissolution;

wherein the nonwoven membrane is obtained by a method characterized in that it comprises the steps of:

(a) electrospinning a solution of one single type of a biocompatible polymer; and (b) simultaneously pouring a suspension of microparticles of at least one therapeutic or cosmetic active agent for obtaining an electrospun nonwoven membrane comprising biocompatible electrospun nanofibers and microparticles of at least one therapeutic or cosmetic active agent entangled between said nanofibers.

2. The nonwoven membrane according to claim 1, characterized in that it comprises at least a first layer comprising biocompatible electrospun nanofibers, a second layer comprising biocompatible electrospun nanofibers and microparticles of at least one therapeutic or cosmetic active agent entangled between the nanofibers; and a third layer comprising biocompatible electrospun nanofibers.

3. The nonwoven membrane according to claim 1, characterized in that the at least one therapeutic or cosmetic active agent has a water solubility of 0.001-33 mg/mL.

4. The nonwoven membrane according to claim 1, characterized in that the microparticles of the at least one therapeutic or cosmetic active agent are microcrystals.

5. The nonwoven membrane according to claim 1, characterized in that the microparticles of the at least one therapeutic or cosmetic active agent have a mean diameter of 0.1-20 µm.

6. The nonwoven membrane according to claim 1, characterized in that the at least one therapeutic or cosmetic active agent is loaded in a percentage of 0.001-20% by weight with respect to the total weight of the nonwoven membrane.

7. The nonwoven membrane according to claim 1, characterized in that the biocompatible electrospun nanofibers have a mean diameter of 50-1000 nm.

8. The nonwoven membrane according to claim 1, characterized in that the biocompatible electrospun nanofibers are composed of one single type of a biocompatible and biodegradable polymer selected from poly-glycolic acid, poly-D,L-lactic acid, poly-D,L-lactide-co-glicolide acid, polycaprolactone, polydioxanone, polyvinylalcohol, collagen, cellulose, hyaluronic acid and a combination thereof.

9. A taylor-made suit comprising the nonwoven membrane according to claim 1 to cover a specific area of a solid tissue.

10. Method for the treatment of tumors that include non-resectable areas with vital vessels; or alternatively for the treatment of surgical borders wherein tumor residues are left; or alternatively for the treatment of osseous tissues with tumor infiltration or positive bone scan; comprising locally applying the taylor-made suit according to claim 9 to the tumors that include non-resectable areas with vital vessels; or alternatively to surgical borders wherein tumor residues are left; or alternatively to osseous tissues with tumor infiltration or positive bone scan, wherein the at least one active agent is a chemotherapeutic agent, in a subject in need thereof.

11. Method for the treatment of a tissue, wherein the treatment comprises the regeneration of the tissue by locally applying the taylor-made suit according to claim 9 to the tissue, wherein the at least one active agent is a chemotherapeutic agent, in a subject in need thereof.

12. A method for the local delivery of a therapeutic or cosmetic active ingredient comprising the step of delivering the therapeutic or cosmetic active ingredient in a controlled and sustained manner comprising the step of applying the nonwoven membrane according to claim 1 to a body area to be treated in a subject in need thereof.

13. A method for the treatment of a specific area of a solid tissue selected from skin, mucosas, bones, muscles, internal organs and solid tumors, comprising applying a taylor-made suit comprising the nonwoven membrane according to claim 1 to the specific area of the solid tissue in a subject in need thereof.

14. The nonwoven membrane according to claim 1, characterized in that the at least one active agent is a therapeutic agent.

15. The nonwoven membrane according to claim 14, characterized in that the therapeutic agent is a chemotherapeutic agent.

16. The nonwoven membrane according to claim 15, characterized in that the chemotherapeutic agent is 7-ethyl-10-hydroxycamptothecin (SN-38).

17. A method for the treatment of tumors that include non-resectable areas with vital vessels; or alternatively for the treatment of surgical borders wherein tumor residues are left; or alternatively for the treatment of osseous tissues with tumor infiltration or positive bone scan; comprising locally applying the nonwoven membrane according to claim 1 to the tumors that include non-resectable areas with vital vessels; or alternatively to the surgical borders wherein tumor residues are left; or alternatively to the osseous tissues with tumor infiltration or positive bone scan, wherein the at least one active agent is a chemotherapeutic agent, in a subject in need thereof.

18. A method for the treatment of a tissue, wherein the treatment comprises the regeneration of the tissue by locally applying the nonwoven membrane according to claim 1 to the tissue, wherein the at least one active agent is a chemotherapeutic agent, in a subject in need thereof.

19. The nonwoven membrane according to claim 1, wherein the active agent is a therapeutic agent selected from the group consisting of: 7-ethyl-10-hydroxycamptothecin (SN-38), paclitaxel, cisplatin, carboplatin, etoposide, carmustine, melphalan, camptothecin, 5-fluorouracil, methotrexate, erlotinib, gefitinib, sunitinib, vandetanib, dasatinib, lapatinib, nutlin, gemcitabine, docetaxel, bortezomib, valproic acid, vismodegib, cinacalcet, trabectedin, topotecan, ((1S,2S,4R)-4-(4-(((S)-2,3-dihydro-1H-inden-1-yl)amino)-7H-pyrrolo [2,3-d]pyrimidin-7-yl)-2-hydroxycyclopentyl) methyl sulfamate (MLN4924), olaparib, iniparib, arsenic trioxide, crizotinib, celecoxib, perifosine, rapamycin, temsirolimus, everolimus, curcumin, resveratrol, genistein, quercetin, chloramphenicol, Penicillin G Procaine, fusidic acid, mebendazol, albendazol, Platelet-derived growth factor (PDGF), Human transforming growth factor-beta (TGF-B), Epidermal growth factor (EGF), Vascular Endothelial Growth Factor (VEGF), Insulin-like Growth Factor I (IGF-I), Basic fibroblast growth factor (bFGF) and Hepatocyte growth factor (HGF).

20. A method for obtaining the nonwoven membrane according to claim 1, characterized in that it comprises the steps of:
(a) electrospinning a solution of one single type of a biocompatible polymer; and
(b) simultaneously pouring a suspension of microparticles of at least one therapeutic or cosmetic active agent for obtaining an electrospun nonwoven membrane comprising biocompatible electrospun nanofibers and microparticles of at least one therapeutic or cosmetic active agent entangled between said nanofibers.

21. The method according to claim 20, characterized in that it comprises the steps of:
(i) at least electrospinning a solution of one single type of a biocompatible polymer for collecting a first layer of a nonwoven membrane comprising biocompatible electrospun nanofibers;
(ii) at least electrospinning a solution of one single type of a biocompatible polymer and simultaneously pouring a suspension of microparticles of at least one therapeutic or cosmetic active agent for collecting over the first layer a second layer of a nonwoven web comprising biocompatible electrospun nanofibers and microparticles of at least one therapeutic or cosmetic active agent entangled between said nanofibers; and
(iii) at least electrospinning a solution of one single type of a biocompatible polymer for collecting over the second layer a third layer of a nonwoven membrane comprising biocompatible electrospun nanofibers.

* * * * *